US 11,684,653 B2

United States Patent
Chang et al.

(10) Patent No.: US 11,684,653 B2
(45) Date of Patent: Jun. 27, 2023

(54) COMPOSITIONS AND METHOD FOR REDUCING VIRULENCE OF MICROORGANISMS

(71) Applicant: The Cleveland Clinic Foundation, Cleveland, OH (US)

(72) Inventors: Eugene Chang, Chicago, IL (US); Jeannette Messer, Chicago, IL (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 0 days.

(21) Appl. No.: 16/807,792

(22) Filed: Mar. 3, 2020

(65) Prior Publication Data
US 2020/0282017 A1 Sep. 10, 2020

Related U.S. Application Data

(60) Provisional application No. 62/821,854, filed on Mar. 21, 2019, provisional application No. 62/814,599, filed on Mar. 6, 2019.

(51) Int. Cl.
| | | |
|---|---|---|
| A61K 38/17 | (2006.01) | |
| A61P 1/00 | (2006.01) | |
| A61K 47/64 | (2017.01) | |
| C12Q 1/02 | (2006.01) | |

(52) U.S. Cl.
CPC .......... *A61K 38/1709* (2013.01); *A61K 47/64* (2017.08); *A61P 1/00* (2018.01); *C12Q 1/025* (2013.01)

(58) Field of Classification Search
CPC .............................. A61K 38/1709; A61P 1/00
See application file for complete search history.

(56) References Cited

U.S. PATENT DOCUMENTS

| | | | | |
|---|---|---|---|---|
| 2008/0038309 A1* | 2/2008 | Fumero | .................... | A61P 27/02 424/423 |
| 2008/0317809 A1* | 12/2008 | Fumero | ..................... | A61P 9/00 514/1.1 |
| 2009/0191253 A2* | 7/2009 | Fumero | ................... | A61P 13/00 514/1.1 |
| 2009/0324677 A1* | 12/2009 | Traversa | .................. | A61P 31/12 424/423 |
| 2010/0152062 A1* | 6/2010 | Harris | ................... | C12Q 1/6883 506/16 |
| 2010/0184625 A1* | 7/2010 | Harris | .................. | C12Q 1/6883 506/17 |
| 2010/0184967 A1* | 7/2010 | Harris | .................. | C12Q 1/6883 536/24.31 |
| 2011/0052493 A1* | 3/2011 | Fumero | ..................... | A61P 9/00 424/9.1 |
| 2013/0137123 A1* | 5/2013 | Cucchiara | .............. | G01N 33/53 435/7.92 |
| 2013/0177560 A1* | 7/2013 | Bieck | ....................... | A61P 25/28 424/134.1 |
| 2013/0183348 A1* | 7/2013 | Taniguchi | ................ | A61P 31/04 424/278.1 |
| 2014/0065094 A1* | 3/2014 | Traversa | .................... | A61P 9/10 424/85.2 |
| 2015/0335763 A1* | 11/2015 | Chavan | ............... | A61K 47/6927 424/490 |
| 2015/0361164 A1* | 12/2015 | Takada | .................... | A61P 13/12 424/133.1 |
| 2018/0353564 A1* | 12/2018 | Tracey | ................. | A61K 31/215 |

OTHER PUBLICATIONS

Agus et al., Understanding host-adherent-invasive *Escherichia coli* interaction in Crohn's disease: opening up new therapeutic strategies. Biomed Res Int. 2014;2014:567929.
Baorto et al., Survival of FimH—expressing enterobacteria in macrophages relies on glycolipid traffic. Nature. Oct. 9, 1997;389(6651):636-9.
Beeley, Peptidomimetics and small-molecule drug design: towards improved bioavailability and in vivo stability. Trends Biotechnol. Jun. 1994;12(6):213-6.
Bird et al., Hydrocarbon double-stapling remedies the proteolytic instability of a lengthy peptide therapeutic. Proc Natl Acad Sci U S A. Aug. 10, 2010;107(32):14093-8.
Bird et al., Synthesis and biophysical characterization of stabilized alpha-helices of BCL-2 domains. Methods Enzymol. 2008;446:369-86.
Bottger et al., Identification of novel mdm2 binding peptides by phage display. Oncogene, 1996, 13, 2141-7.
Bottger et al., Molecular characterization of the hdm2-p53 interaction. J Mol Biol. Jun. 27, 1997;269(5):744-56.
Brinckerhoff et al., Terminal modifications inhibit proteolytic degradation of an immunogenic MART-1(27-35) peptide: implications for peptide vaccines. Int J Cancer. Oct. 29, 1999;83(3):326-34.
Chandrudu et al., Chemical methods for peptide and protein production. Molecules. Apr. 12, 2013;18(4):4373-88.
Chassaing et al., Crohn disease—associated adherent—invasive *E. coli* bacteria target mouse and human Peyer's patches via long polar fimbriae. J Clin Invest. Mar. 2011;121(3):966-75.
Cutler et al., Targeted sarcoplasmic reticulum Ca2+ ATPase 2a gene delivery to restore electrical stability in the failing heart. Circulation. Oct. 23, 2012;126(17):2095-104.
Cwirla et al., Peptides on phage: a vast library of peptides for identifying ligands. Proc. Natl. Acad. Sci. USA, 1990, 87, 6378-82.
Dalal et al., The microbial basis of inflammatory bowel diseases. J Clin Invest. Oct. 2014;124(10):4190-6.
Dasgupta et al., N-terminal acylation of somatostatin analog with long chain fatty acids enhances its stability and anti-proliferative activity in human breast adenocarcinoma cells. Biol Pharm Bull. Jan. 2002;25(1):29-36.
Davidson et al., Chronic colitis in IL-10-/- mice: insufficient counter regulation of a Th1 response. Int Rev Immunol. 2000;19(1):91-121.

(Continued)

*Primary Examiner* — Amber D Steele
(74) *Attorney, Agent, or Firm* — Casimir Jones, SC; David W. Staple

(57) ABSTRACT

The present disclosure relates to compositions and methods for reducing virulence of microorganisms. In particular, the present invention provides HMGB1 and variants and mimetics thereof for use in reducing virulence of microorganisms (e.g., in disease).

9 Claims, 15 Drawing Sheets

Specification includes a Sequence Listing.

(56) References Cited

OTHER PUBLICATIONS

Devlin et al., Random peptide libraries: a source of specific protein binding molecules. Science. Jul. 27, 1990;249(4967):404-6.

Dower, Targeting growth factor and cytokine receptors with recombinant peptide libraries. Curr Opin Chem Biol. Jun. 1998;2(3):328-34.

Dreux et al., Point mutations in FimH adhesin of Crohn's disease-associated adherent-invasive *Escherichia coli* enhance intestinal inflammatory response. PLoS Pathog. Jan. 2013;9(1):e1003141.

Ellman et al., Biosynthetic method for introducing unnatural amino acids site-specifically into proteins. Methods Enzymol. 1991;202:301-36.

Gentilucci et al., Chemical modifications designed to improve peptide stability: incorporation of non-natural amino acids, pseudo-peptide bonds, and cyclization. Curr Pharm Des. 2010;16(28):3185-203.

Georgiadis et al., Polysialic acids: potential in improving the stability and pharmacokinetics of proteins and other therapeutics. Cell Mol Life Sci. Dec. 2000;57(13-14):1964-9.

Glasser et al., Adherent invasive *Escherichia coli* strains from patients with Crohn's disease survive and replicate within macrophages without inducing host cell death. Infect Immun. Sep. 2001;69(9):5529-37.

Green et al., N-terminal His(7)—modification of glucagon-like peptide—1(7-36) amide generates dipeptidyl peptidase IV-stable analogues with potent antihyperglycaemic activity. J Endocrinol. Mar. 2004;180(3):379-88.

Ha et al., Mechanistic links between gut microbial community dynamics, microbial functions and metabolic health. World J Gastroenterol. Nov. 28, 2014;20(44):16498-517.

Haiko et al., The role of the bacterial flagellum in adhesion and virulence. Biology (Basel). Oct. 25, 2013;2(4):1242-67.

Hardman et al., Structure of the A-domain of HMG1 and its interaction with DNA as studied by heteronuclear three- and four-dimensional NMR spectroscopy. Biochemistry. Dec. 26, 1995;34(51):16596-607.

Harris. Somatostatin and somatostatin analogues: pharmacokinetics and pharmacodynamic effects. Gut. 1994;35(3 Suppl):S1-4.

Heya et al., Controlled release of thyrotropin releasing hormone from microspheres: evaluation of release profiles and pharmacokinetics after subcutaneous administration. J Pharm Sci. Jun. 1994;83(6):798-801.

Hodgson et al., The synthesis of peptides and proteins containing non-natural amino acids. Chem Soc Rev. Sep. 10, 2004;33(7):422-30.

Hojo, Recent progress in the chemical synthesis of proteins. Curr Opin Struct Biol. Jun. 2014;26:16-23.

Huttenhower et al., Structure, function and diversity of the healthy human microbiome. Nature. Jun. 13, 2012;486(7402):207-14.

Jacobsen et al., Stapling of a 3(10)—helix with click chemistry. J Org Chem. Mar. 4, 2011;76(5):1228-38.

Kieber-Emmons et al., Therapeutic peptides and peptidomimetics. Curr Opin Biotechnol. Aug. 1997;8(4):435-41.

Kim et al., Introduction of all-hydrocarbon i,i+3 staples into alpha-helices via ring-closing olefin metathesis. Org Lett. Jul. 2, 2010;12(13):3046-9.

Klemm et al., Prevention of bacterial adhesion. Appl Microbiol Biotechnol. Sep. 2010;88(2):451-9.

Klemm et al., Type 1 Fimbriae, Curli, and Antigen 43: Adhesion, Colonization, and Biofilm Formation. EcoSal Plus. Dec. 2004;1(1).

Krebs et al., Enantioselective synthesis of non-natural aromatic alpha-amino acids. Chemistry. Jan. 23, 2004;10(2):544-53.

MacPherson et al., The habitat, double life, citizenship, and forgetfulness of IgA. Immunol Rev. Jan. 2012;245(1):132-46.

Madden et al., Facile synthesis of stapled, structurally reinforced peptide helices via a photoinduced intramolecular 1,3-dipolar cycloaddition reaction. Chem Commun (Camb). Oct. 7, 2009;(37):5588-90.

McCauley et al., Three cheers for the goblet cell: maintaining homeostasis in mucosal epithelia. Trends Mol Med. Aug. 2015;21(8):492-503.

Merga et al., Mucosal barrier, bacteria and inflammatory bowel disease: possibilities for therapy. Dig Dis. 2014;32(4):475-83.

Merrifield. Solid Phase Peptide Synthesis. I. The Synthesis of a Tetrapeptide. J. Am. Chem. Soc. 1963. 85 (14): 2149-2154.

Mitchell et al., A new synthetic route to tert-butyloxycarbonylaminoacyl-4-(oxymethyl)phenylacetamidomethyl-resin, an improved support for solid-phase peptide synthesis. J. Org. Chem. 1978. 43 (13): 2845-2852.

Moore. Designing peptide mimetics. Trends Pharmacol Sci. Apr. 1994;15(4):124-9.

Morgan et al., Biodiversity and functional genomics in the human microbiome. Trends Genet. Jan. 2013;29(1):51-8.

Mossman et al., Cutting edge: FimH adhesin of type 1 fimbriae is a novel TLR4 ligand. J Immunol. Nov. 15, 2008;181(10):6702-6.

Noren et al., A general method for site-specific incorporation of unnatural amino acids into proteinds. Science, 1989, 244, 182.

Ofek et al., Mannose binding and epithelial cell adherence of *Escherichia coli*. Infect Immun. Oct. 1978;22(1):247-54.

Orndorff et al., Organization and expression of genes responsible for type 1 piliation in *Escherichia coli*. J Bacteriol. Aug. 1984;159(2):736-44.

Palone et al., Role of HMGB1 as a suitable biomarker of subclinical intestinal inflammation and mucosal healing in patients with inflammatory bowel disease. Inflamm Bowel Dis. Aug. 2014;20(8):1448-57.

Peterson et al., Intestinal epithelial cells: regulators of barrier function and immune homeostasis. Nat Rev Immunol. Mar. 2014;14(3):141-53.

Powell et al., Peptide stability in drug development. II. Effect of single amino acid substitution and glycosylation on peptide reactivity in human serum. Pharm Res. Sep. 1993;10(9):1268-73.

Pratt et al., Genetic analysis of *Escherichia coli* biofilm formation: roles of flagella, motility, chemotaxis and type I pili. Mol Microbiol. Oct. 1998;30(2):285-93.

Ramakers et al., Molecular tools for the construction of peptide-based materials. Chem Soc Rev. Apr. 21, 2014;43(8):2743-56.

Ramon et al. PEGylated interferon-alpha2b: a branched 40K polyethylene glycol derivative. Pharm Res. Aug. 2005;22(8):1374-86.

Rhodes. The role of *Escherichia coli* in inflammatory bowel disease. Gut. May 2007;56(5):610-2.

Sartor et al., Intestinal microbes in inflammatory bowel diseases. Am J Gastroenterol Suppl. 2012;1(1):15-21.

Scott et al., Searching for peptide ligands with an epitope library. Science. Jul. 27, 1990;249(4967):386-90.

Sidhu et al., Phage display for selection of novel binding peptides. Methods Enzymol. 2000;328:333-63.

Small et al., Persistent infection with Crohn's disease-associated adherent-invasive *Escherichia coli* leads to chronic inflammation and intestinal fibrosis. Nat Commun. 2013;4:1957.

Strober et al., Adherent-invasive *E. coli* in Crohn disease: bacterial "agent provocateur". J Clin Invest. Mar. 2011;121(3):841-4.

Sulochana et al., Developing antiangiogenic peptide drugs for angiogenesis-related diseases. Curr Pharm Des. 2007;13(20):2074-86.

Turner. Intestinal mucosal barrier function in health and disease. Nat Rev Immunol. Nov. 2009;9(11):799-809.

Verdine et al., Stapled peptides for intracellular drug targets. Methods Enzymol. 2012;503:3-33.

Vitali et al., Fecal HMGB1 is a novel marker of intestinal mucosal inflammation in pediatric inflammatory bowel disease. Am J Gastroenterol. Nov. 2011;106(11):2029-40.

Wang et al., Functions of Antimicrobial Peptides in Gut Homeostasis. Curr Protein Pept Sci. 2015;16(7):582-91.

Weir et al., Structure of the HMG box motif in the B-domain of HMG1. EMBO J. Apr. 1993;12(4):1311-9.

White et al., Replacing amino acids in translation: expanding chemical diversity with non-natural variants. Methods. Mar. 15, 2013;60(1):70-4.

(56) References Cited

OTHER PUBLICATIONS

Zetterstrom et al., High mobility group box chromosomal protein 1 (HMGB1) is an antibacterial factor produced by the human adenoid. Pediatr Res. Aug. 2002;52(2):148-54.
Zhu et al., Cytosolic HMGB1 controls the cellular autophagy/apoptosis checkpoint during inflammation. J Clin Invest. Mar. 2, 2015;125(3):1098-110.

* cited by examiner

FIG. 1E
HMGB1^(f/f)
FIG. 1F
HMGB1^(f/f, Vil-CRE)
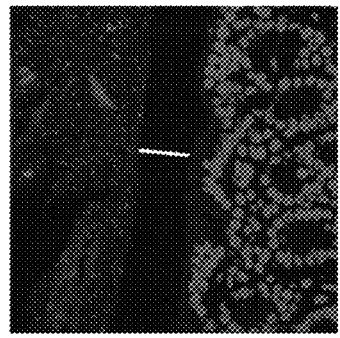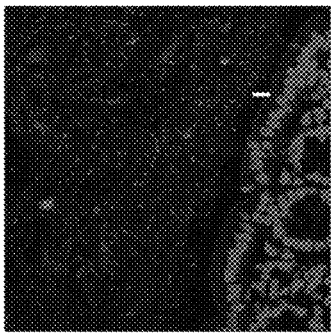
FIG. 1G
16S rRNA in 1 cm of tissue
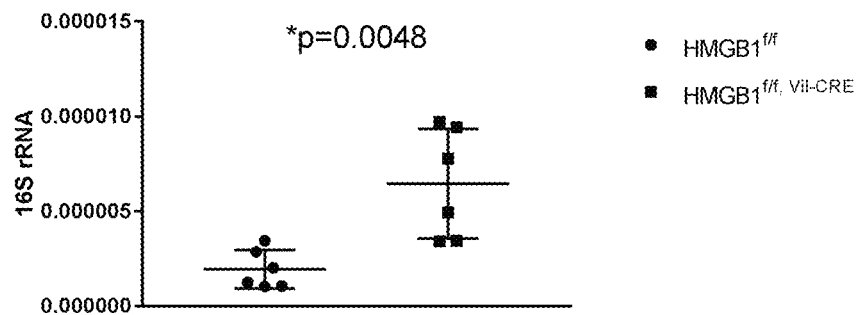
FIG. 1H
HMGB1^(f/f)
FIG. 1I
HMGB1^(f/f, Vil-CRE)
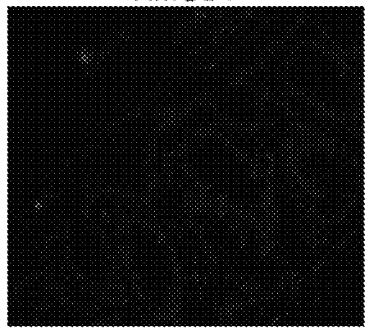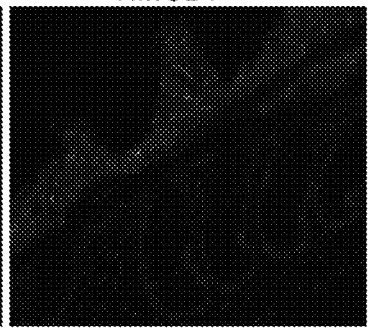
Male
Female

FIG. 2A

CAMo-1: [S/T]xExP

FIG. 2B

FACKTANGTAIPIGGGSANVYVNLA
PVVNVGQNLVVDLSTQIFCHNDYPE
TITDYVTLQRGSAYGGVLSNFSGTV
KYSGSSYPFPT▇▇▇▇RVVYNSRTD
KPWPVALYLTPVSSAGGVAIKAGSL
IAVLILRQTNNYNSDDFQFVWNIYA
NNDVVVPT

FIG. 2C

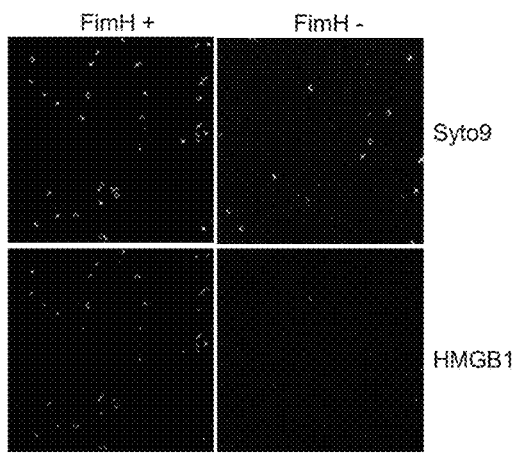

FIG. 2D

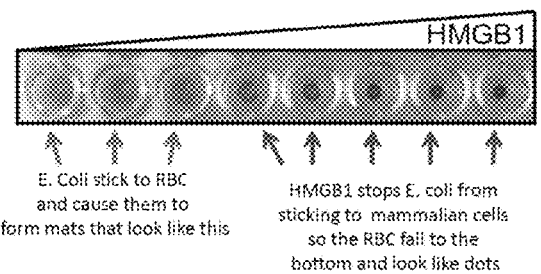

E. Coli stick to RBC and cause them to form mats that look like this

HMGB1 stops E. coli from sticking to mammalian cells so the RBC fall to the bottom and look like dots FIG. 2E  
E. coli alone
FIG. 2F  
E. coli +HMGB1
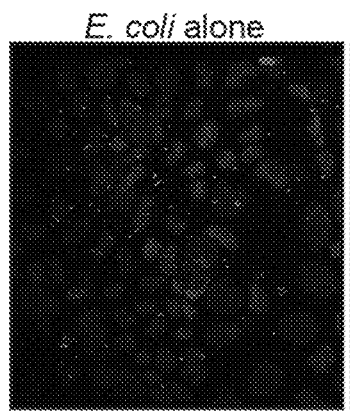
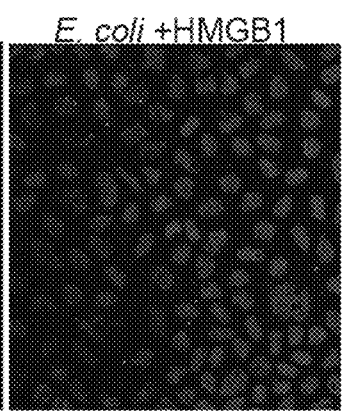
FIG. 2G
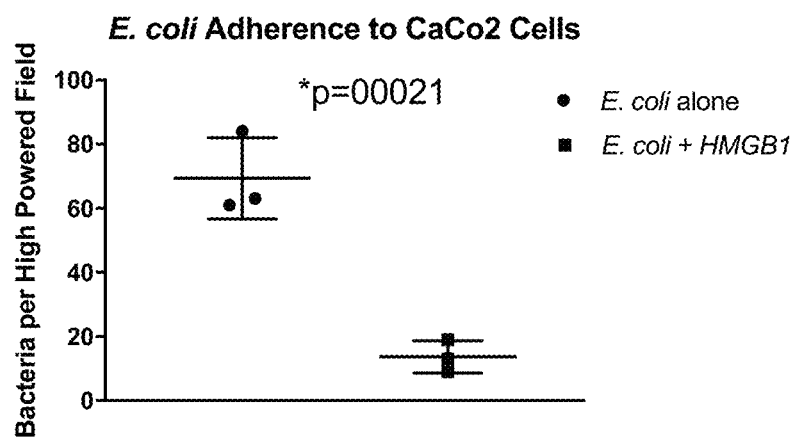

Box A targeting *E. coli*

Box A coating *E. coli*

FIG. 6A
Healthy
FIG. 6B
Inflammatory bowel disease
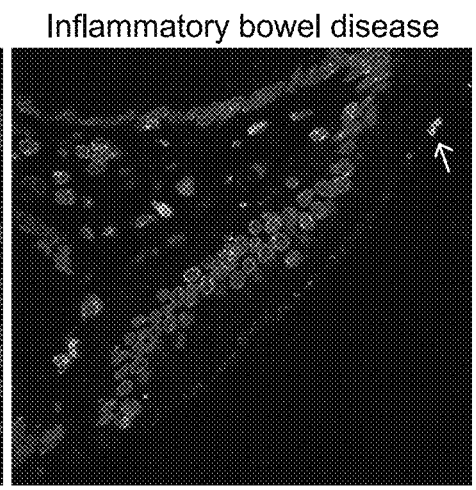
FIG. 6C
Non-IBD Control
FIG. 6D
Ulcerative Colitis
FIG. 6E
Crohn's Disease
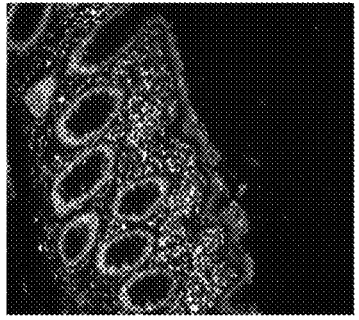 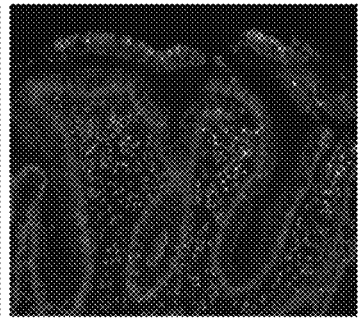 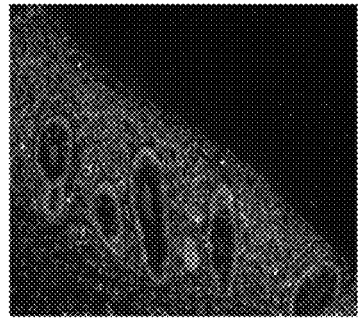
20x
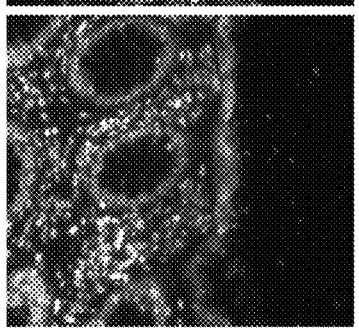 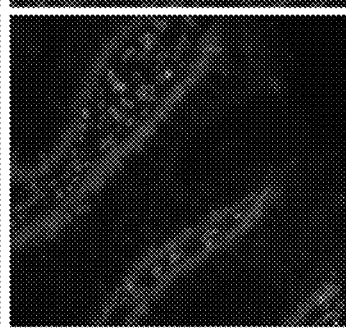 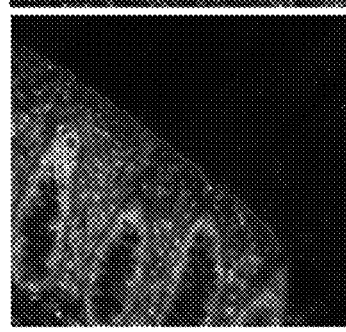
40x Non-IBD Control Ulcerative Colitis Crohn's Disease

```
MGKGDPKKPR GKMSSYAFFV QTCREEHKKK HPDASVNFSE FSKKCSERWK TMSAKEKGKF
EDMAKADKAR YEREMKTYIP PKGETKKKFK DPNAPKRPPS AFFLFCSEYR PKIKGEHPGL
SIGDVAKKLG EMWNNTAADD KQPYEKKAAK LKEKYEKDIA AYRAKGKPDA AKKGVVKAEK
SKKKKEEEED EEDEEDEEEE EDEEDEDEEE DDDDE (SEQ ID NO: 1)
```

FIG. 8B

```
TCREEHKKKH PDASVNFSEF SKKCSERWKT MSAKEKGKFE DMAKA (SEQ ID NO: 2)
```

FIG. 8C

```
GKGDPKKPRGKMSSYAFFVQTCREEHKKKHPDASVNFSEFSKKCSERWKTMSAKEKGKFEDMAKADKARY
EREMKTYIPPKGETKKKFKDPNAPKRP (SEQ ID NO: 3)
```

COMPOSITIONS AND METHOD FOR REDUCING VIRULENCE OF MICROORGANISMS

STATEMENT REGARDING FEDERAL FUNDING

This invention was made with government support under DK114713 National Institutes of Health. The government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 5,099 Byte ASCII (Text) file named "37593-203_ST25.TXT," created on Feb. 8, 2022.

FIELD OF THE INVENTION

The present disclosure relates to compositions and methods for reducing virulence of microorganisms. In particular, the present invention provides HMGB1 and variants and mimetics thereof for use in reducing virulence of microorganisms (e.g., in disease).

BACKGROUND OF THE INVENTION

Diseases caused or exacerbated by microorganisms affect hundreds of millions of patients each year. These diseases range from acute, life-threatening infections to chronic inflammatory diseases and result in staggering societal and economic losses across all age groups and ethnicities. The microorganisms involved in these diseases can be, for example, bacteria and many are initially normal body residents. Disease-causing microorganisms express virulence mechanisms that include appendages for attachment to tissues and secreted products such as toxins. Expression of these virulence mechanisms then leads to damage to body tissues and activation of the immune system. Both pathogenic and commensal microbes can produce virulence mechanisms and these are the major determinants of the clinical course and outcomes of diseases involving microorganisms.

The current therapies for microbe-related diseases are focused on killing pathogenic microbes or inhibiting their replication. However, these therapies often kill microbes fairly indiscriminately and with various efficacies, depending upon the microbe in question. This means that the treatments themselves can contribute to disease by inadvertently killing beneficial microbes or by exacerbating immune activation through release of pro-inflammatory components of dead or dying microbes. In most cases, the only way to determine whether anti-microbial therapy is successful is to document elimination of a specific microbial population through culture or nucleic acid based detection methods. However, when the disease is the result of activation of virulence in normally commensal microbes, this is not feasible.

Treatments directed at microbes are particularly problematic in chronic inflammatory diseases that have a microbial component. These types of diseases include cancers, metabolic diseases, arthritis, and inflammatory bowel diseases. Current treatments for these diseases are primarily focused on the immune component of disease because the microbial targets are poorly defined and are likely to be normally commensal bacteria. These immune-directed treatments are often ineffective and lead to significant side effects, including immunosuppression. This means that there are urgent, unmet needs to develop novel therapies that suppress microbial virulence mechanisms in pathogenic or commensal microbes and to develop methods to characterize and monitor expression of virulence mechanisms in microorganisms in order to improve diagnosis and treatment of these diseases.

Inflammatory bowel diseases are one group of microbe-related chronic inflammatory diseases. Patients suffering from inflammatory bowel diseases (IBD) experience varying degrees of abdominal discomfort throughout their digestive tract. The pathophysiology of these diseases is a confluence of microbial and genetic factors. IBD affects approximately 1.6 million patients in the United States of which 80,000 of those are children. This results in a staggering direct cost for patient-related issues that ranges from $11-28 billion annually. However, a specific form of IBD, namely Crohn's Disease (CD), is more menacing and presents dire consequences even if timely medical intervention is initiated. CD affects a wide swath of ethnicities but is more common in Caucasian and African-American populations, less common in Latino and Asian populations, and people of Ashkenazi descent are at 4-5 fold higher risk than the general population.

CD typically affects the entire length and circumference of the small intestine and the upper large intestine. The disease manifests itself in the form of patchy lesions that are sporadically located along the intestines and penetrate the full thickness of the tissue itself. At the onset of the disease, the intestinal tissue progresses through several stages of inflammation which becomes increasingly worse over time. In normal situations, the body uses the inflammatory response to combat a variety of foreign insults as well as participate in body homeostasis at multiple levels. However, when the inflammatory response becomes unmanageable by the body, due to a number of factors, severe tissue damage and/or tissue death occurs. Manifestations of the disease include continual abdominal pain, bleeding and tissue rupturing, nutrient malabsorption, poor overall body growth and development, repeated surgical procedures, and the potential of intestinal cancer. Quality of life issues relating to CD range from depression, negative body image issues and social stigmas, and the negative impact on professional and family lifestyles. These attributes further contribute to the overall deterioration of this patient population.

Treatment options available to CD patients range from prescribed oral medications to biological reagents specifically designed to combat the hyperactive inflammatory response. However, a large percentage of the CD population responds poorly to these treatment options, if at all. Further problems with current treatment options are that they are quite expensive, are inefficient, and have numerous side effects including the potential of inducing different types of cancer. CD patients experience recurrent flare-ups and typically require a highly invasive surgery to remove the dying or dead tissue. It is estimated that 70% of those with CD will require surgery over their lifetime and 30% and 60% of those will require additional surgery at 3 and 10 years post-initial surgery, respectively. Therefore, there is an unmet clinical need to address the issues surrounding the highly pro-inflammatory local environment in CD patients through therapies targeted at the microbial component of the disease.

SUMMARY OF THE INVENTION

The present disclosure relates to compositions and methods for reducing virulence of microorganisms. In particular, the present invention provides HMGB1 and variants and mimetics thereof for use in reducing virulence of microorganisms (e.g., in disease).

For example, in some embodiments, the present invention provides a method of treating or preventing microbial virulence, comprising: administering a HMGB1 polypeptide or fragment or mimetic thereof to a subject, wherein said administering prevents or treats microbial virulence in the subject. In some embodiments, the HMGB1 polypeptide or fragment or mimetic binds to the motif [S/T]-x-E-x-P in a microbial protein. In some embodiments, the HMGB1 polypeptide or fragment or mimetic binds to Escherichia coli (E. coli) FimH protein. In some embodiments, the HMGB1 polypeptide or fragment or mimetic is a peptide. In some embodiments, the HMGB1 polypeptide or fragment or mimetic comprises at least one amino acid change relative to wild type HMGB1. In some embodiments, the HMGB1 peptide is the peptide of SEQ ID NO:2. In some embodiments, the microbe is a bacteria. In some embodiments, the HMGB1 polypeptide or fragment or mimetic is conjugated to a drug (e.g., an antimicrobial drug). In some embodiments, the administering treats a disease. In some embodiments, the disease is a chronic inflammatory disease or an infectious disease (e.g., including, but not limited to, inflammatory bowel disease, rheumatoid arthritis, non-alcoholic fatty liver disease, type II diabetes, urinary tract infections, pneumonia, or sepsis).

Further embodiments provide a method of treating or preventing a disease, comprising: administering a HMGB1 polypeptide or fragment or mimetic thereof to a subject, wherein the administering prevents or treats a disease in the subject.

Yet other embodiments provide the use of a HMGB1 polypeptide or fragment or mimetic thereof to treat or prevent microorganism virulence or disease in a subject.

Still other embodiments provide a composition comprising a HMGB1 polypeptide or fragment or mimetic thereof and a pharmaceutically acceptable carrier.

Additional embodiments provide a composition comprising a HMGB1 polypeptide or fragment or mimetic thereof and a pharmaceutically acceptable carrier for use in treating or preventing microorganism virulence or disease in a subject.

Certain embodiments provide a method of characterizing microbial virulence in a subject, comprising: a) contacting a sample from said subject comprising microorganisms with a HMGB1 polypeptide or fragment or mimetic; and b) determining the level of binding of the HMGB1 polypeptide or fragment or mimetic to the microorganisms in the sample. In some embodiments, the absence or decrease in binding of the HMGB1 polypeptide or fragment or mimetic to the microorganism is indicative of disease in the subject. In some embodiments, the subject is administered a treatment (e.g., an antimicrobial agent or an anti-inflammatory agent) prior or after the method. In some embodiments, the method is repeated after administration of the treatment. In some embodiments, the method further comprising the step of identifying microorganisms that bind to the HMGB1 polypeptide or fragment or mimetic. In some embodiments, the HMGB1 polypeptide or fragment or mimetic is labeled (e.g., fluorophore).

Additional embodiments are described herein.

DESCRIPTION OF THE FIGURES

FIGS. 1E and 1F are images of fluorescent in situ hybridization (FISH) using eubacterial probes on Carnoy's fixed sections of colons from HMGB1$^{f/f}$ (FIG. 1E) and HMGB1$^{f/f,\ Vil-CRE}$ mice (FIG. 1F). White lines indicate separation between microbes and host epithelium. In some areas in HMGB 1$^{f/f,\ Vil-CRE}$ mice there is essentially no separation. FIG. 1G is a graph showing results of q-PCR for the 16S rRNA gene in mucosal scrapings. FIGS. 1H and 1I are immunofluorescent images of Carnoy's-fixed colons from HMGB 1$^{f/f}$ (FIG. 1H) and HMGB1$^{f/f,\ Vil-CRE}$ mice (FIG. 1I) stained with an anti-fungal antibody that broadly recognizes commensal fungi found in the gut. HMGB1 deficient mice have increased numbers of fungi and the fungi are found in close proximity to the mucosal surface.

FIG. 2A shows that the CAMo-1 motif is composed of conserved and variable (X) amino acids. FIG. 2B is the amino acid sequence of the mannose binding domain of E. coli FimH with CAMo-1 highlighted (SEQ ID NO: 4). FIG. 2C is an image of immunofluorescence microscopy of E. coli+/− FimH exposed to recombinant HMGB1 protein and stained with Syto9 to identify bacteria and anti-HMGB1 antibody. FIG. 2D is an image of a red blood cell (RBC) agglutination assay with FimH+E. coli (K12) and increasing amounts of recombinant HMGB1 (highest concentration 5 µM). HMGB1 blocks E. coli binding to RBC and prevents agglutination which leads to RBC sedimentation (appearance of a dot). FIGS. 2E and 2F are fluorescent images of CaCo2 cells were exposed to wild type untreated E. coli (K12) (FIG. 2E) or E. coli (K12) treated with recombinant human HMGB1 (FIG. 2F). FIG. 2G is a graph showing that exposure to HMGB1 significantly reduced the number of adherent bacteria.

FIG. 4A shows disruption of FimH from *E. coli* (Gram– bacterium) binding to mannose. FIG. 4B shows disruption of Asa1 from *Enterococcus faecalis* (Gram+ bacterium) binding to fibronectin. FIG. 4C shows disruption of hemagglutinin from Influenza B (–ss RNA virus) binding to sialic acid. FIG. 4D shows disruption of VSP4A1 from Giardia intestinalis (protozoal parasite) binding to fibronectin.

FIGS. 6A and 6B show immunofluorescent microscopy of HMGB1 (healthy and arrow in diseased) and *E. coli* FimH (diseased only) in endoscopic biopsies from healthy and diseased gut (inflammatory bowel disease). FIGS. 6C-6E show immunofluorescent microscopy of HMGB1 staining in sections of resected colon from non-IBD (FIG. 6C), ulcerative colitis (FIG. 6D), and Crohn's disease (FIG. 6E) patients.

FIGS. 8A-8C show the amino acid sequences of full length HMGB1 (FIG. 8A; SEQ ID NO: 1), an exemplary HMGB1 peptide (FIG. 8B; SEQ ID NO: 2), and a fragment of HMGB1 comprising amino acids 2-97 (Box A) (FIG. 8C; SEQ ID NO: 3).

DEFINITIONS

Figures 1A, 1B:
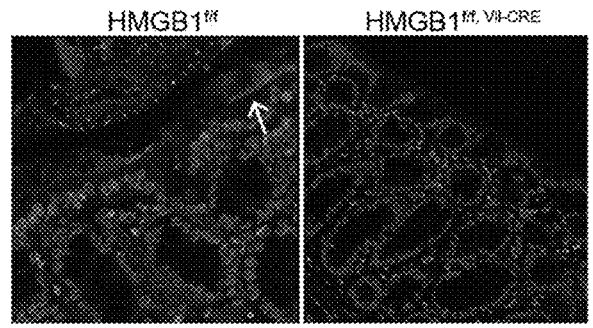
FIGS. 1A and 1B are immunofluorescence images showing that HMGB1 plays a physiologic role in gut antimicrobial defense. HMGB1 staining is shown in Carnoy's fixed colons from HMGB1$^{f/f}$ (wild type) mice (FIG. 1A) and HMGB 1$^{f/f,\ Vil-CRE}$ (deficient in HMGB1 only in intestinal epithelial cells) mice (FIG. 1B). The mucosal surface is denoted by the white arrow.

To facilitate an understanding of the present invention, a number of terms and phrases are defined below.

As used herein, the term "subject" refers to organisms to be treated by the methods of embodiments of the present invention. Such organisms preferably include, but are not limited to, mammals (e.g., murines, simians, equines, bovines, porcines, canines, felines, and the like), and most preferably includes humans. In the context of the invention, the term "subject" generally refers to an individual who will receive or who has received treatment (e.g., administration of a protein or peptide of the present invention and optionally one or more other agents) for disease (e.g., inflammatory disease) or other condition requiring treatment.

The term "diagnosed," as used herein, refers to the recognition of a disease by its signs and symptoms (e.g., resistance to conventional therapies), or genetic analysis, pathological analysis, histological analysis, diagnostic assay (e.g., for disease) and the like.

As used herein the term, "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reaction that occur within a natural environment.

As used herein, the term "host cell" refers to any eukaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

As used herein, the term "effective amount" refers to the amount of a therapeutic agent (e.g., a protein or peptide of the present invention) sufficient to effect beneficial or desired results. An effective amount can be administered in one or more administrations, applications or dosages and is not intended to be limited to a particular formulation or administration route.

As used herein, the term "co-administration" refers to the administration of at least two agent(s) (e.g., a protein or peptide of the present invention) or therapies to a subject. In some embodiments, the co-administration of two or more agents/therapies is concurrent. In some embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "toxic" refers to any detrimental or harmful effects on a cell or tissue as compared to the same cell or tissue prior to the administration of the toxicant.

As used herein, the term "virulence" as in "microbial virulence" refers to the degree of damage (e.g., level of disease) caused by a microbe (e.g., bacteria) to its host (e.g., subject). In some embodiments, virulence of a microbe is related to its intrinsic virulence factors. The virulence factors of bacteria are typically, for example, proteins or other molecules that enable bacteria to cause disease. For example, virulence factors can be adhesion proteins or toxins.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

The term "sample" as used herein is used in its broadest sense. A sample may comprise a cell, tissue, or fluids, fecal or stool samples, nucleic acids or polypeptides isolated from a cell, and the like.

As used herein, the terms "purified" or "to purify" refer, to the removal of undesired components from a sample. As used herein, the term "substantially purified" refers to molecules that are at least 60% free, preferably 75% free, and most preferably 90%, or more, free from other components with which they usually associated.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "test compound" refers to any chemical entity, pharmaceutical, drug, and the like, that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by using the screening methods of the present invention. A "known therapeutic compound" refers to a therapeutic compound that has been shown (e.g., through animal trials or prior experience with administration to humans) to be effective in such treatment or prevention. In some embodiments, "test compounds" are agents that treat or prevent disease (e.g., inflammatory disease).

DETAILED DESCRIPTION OF THE INVENTION

The present disclosure relates to compositions and methods for reducing virulence of microorganisms. In particular, the present invention provides HMGB1 and variants and mimetics thereof for use in reducing virulence of microorganisms (e.g., in disease).

Microbial virulence mechanisms cause or significantly contribute to a number of infectious and inflammatory diseases. Inflammatory bowel diseases (IBD) exemplify this type of disease. The current paradigm for IBD etiopathophysiology is inappropriate activation of intestinal mucosal immune responses (1). Several lines of evidence have converged on bacteria as the trigger for these responses (2). However, the mechanisms through which bacteria contribute to initiation or perpetuation of immune responses and mucosal damage in IBD are poorly characterized and represent a critical gap in knowledge. This gap is especially critical since current IBD therapies are ineffective at achieving sustained remission or cure and IBD not only significantly impacts health and quality of life, but also increases the risk of life-threatening colorectal cancer. Therefore, this gap in knowledge is a critical barrier to the development of effective treatments for IBD and there is an urgent unmet need to determine how bacteria contribute to IBD, develop a biomarker to monitor this contribution, and provide appropriate treatment.

Experiments described herein describe that HMGB1-regulation of microbial virulence is defective in IBD and can be used as a biomarker to characterize disease severity and predict response to therapy.

Three major mechanisms have been proposed for how bacteria could contribute to aberrant intestinal mucosal immune responses such as those in IBD. The first is that IBD is caused by infection with a true pathogen (1). A true pathogen is an infectious agent that causes disease in virtually any susceptible host. Opportunistic pathogens are potentially infectious agents that rarely cause disease in individuals unless an event causes dysbiosis in a subject that makes the subject susceptible to disease caused by the opportunistic pathogen. Evidence for this mechanism is scant, but Adherent Invasive *E. coli* (AIEC) have been proposed to be just such a pathogen and have been implicated in ileal Crohn's disease (3-7). Similarly, patients with both Crohn's disease and ulcerative colitis have increased numbers of mucosal adherent *E. coli* in their intestine and *E. coli* recovered from patients with IBD often have mutations in the mannose-binding domain of the adherence protein fimbrial protein H (FimH) (8,9). FimH sits at the tip of type I fimbrae and mediates attachment of *E. coli* and other bacteria to mammalian cells (10). It is also an important bacterial component for biofilm formation since fimbrae can stick to surfaces or secreted components from other bacteria (11). FimH is a phase variable gene and expression is tightly regulated in response to the microbial environment (10). The second proposed mechanism is that dysbiosis, or an alteration to the structure of the bacterial community, causes IBD (12). Investigations into this mechanism have been complicated by the fact that there is a great deal of taxonomic diversity between individuals and consistent changes to microbial populations related to disease have been difficult to identify (13,14). It is also not clear whether dysbiosis is a cause or effect of disease since inflammation can itself lead to changes in bacterial community composition in the gut. Lastly, failure of host antimicrobial defense systems has been proposed as a cause of bacterial-dependent pathology in IBD (15). This mechanism of IBD pathology is heavily supported by evidence from murine models utilizing genetic knockouts of host antimicrobial defense components, genetic polymorphisms in bacterial sensing and response mechanisms associated with IBD risk in GWAS studies, and increased titers of antibodies targeting gut commensal bacterial proteins such as *E. coli* outer membrane porin C (OmpC) in patients with IBD (1). This mechanism could also potentially account for increased incidence of commensal bacteria that appear to have acquired virulence and dysbiosis if normal host mechanisms that regulate colonization, survival, and virulence of bacteria in the gut are altered.

Host antimicrobial defense systems create physical and chemical barriers between the microbes in the gut lumen and host tissues. These systems are primarily deployed by intestinal epithelial cells (IEC) in response to innate immune sensing of microbes in the gut (16). These cells physically bar bacteria from accessing underlying tissues with their cell bodies and tightly interconnected structure (17). Goblet cells, a specialized type of IEC, produce mucus that physically separates microbes from the host cell surface (18). Intestinal epithelial cells also produce antimicrobial peptides, which kill a broad class of microbes seemingly indiscriminately (19). Finally, IEC transport secretory IgA produced by plasma cells in the lamina propria into the gut lumen. This immunoglobulin coats bacteria in the intestine and promotes colonization by non-pathogenic bacteria while also limiting inflammatory responses to bacteria (20). When any of these IEC-mediated antimicrobial defenses are compromised, the types and location of bacteria within the intestine change and the host becomes more susceptible to colitis (16). These factors indicate that host antimicrobial defense systems and IEC are pivotal in the bacterial-mediated aberrant intestinal mucosal immune responses seen during IBD.

Accordingly, provided herein are HMGB1 polypeptides or fragments or mimetics thereof for use in diagnostic, screening, and therapeutic applications related to infectious or inflammatory diseases.

Inflammatory bowel diseases (IBD) exemplify this type of disease. However, the present invention is not limited to IBD related applications. The compositions and methods described herein find use in applications related to a variety of infectious and inflammatory diseases as described herein.

I. HMGB1

High mobility group box 1 (HMGB1) is a multifunctional protein that is produced in IEC in response to innate immune sensing of microbes. HMGB1 has three major structural domains: two DNA binding motifs, referred to as "Box A" and "Box B" motifs, and an acidic carboxyl terminus. The Box A and Box B motifs are 70 to 80 amino acid L-shaped domains formed by three α-helical segments that are important for DNA binding (Weir et al., *EMBO J.*, 12(4): 1311-9 (1993); and Hardman et al., *Biochemistry*, 34(51): 16596-607 (1995)). HMGB1 binds to the minor groove of DNA through hydrophobic amino acids that expand the groove and facilitate the unwinding and bending of DNA, allowing formation of nucleoprotein complexes that enhance the activity of several transcription factors. HMGB1 is decreased in tissues from patients with active IBD and loss of HMGB1 from IEC leads to increased susceptibility to colitis in mouse models (21). It is also found in stool and concentrations in stool increase during active IBD (22,23). HMGB1 is localized to colonic mucus under normal, physiologic conditions and loss of HMGB1 from this compartment leads to dysbiosis and loss of the physical barrier between bacteria and host epithelial tissues. An HMGB1 interaction motif has been identified in the *E. coli* FimH protein through which HMGB1 specifically interacts with this protein. When *E. coli* expressing FimH are exposed to HMGB1, they are no longer able to adhere to mammalian cells. This indicates that HMGB1 binds to a phase variable virulence gene of a normally commensal microbe and inactivates that virulence mechanism. This is significant because it is a completely novel function for this protein and identifies a new mechanism of host antimicrobial defense with direct relevance for IBD. It also identifies HMGB1 targeting as a biomarker of microbial virulence in the gut.

Experiments described herein demonstrate that high mobility group box 1 (HMGB1) binds to a specific amino acid motif {[S/T]-x-E-x-P} found in a number of bacterial, fungal, viral, and protozoal proteins. Many of these proteins are expressed on the surface of microbes and are associated with microbial virulence and human and animal disease pathophysiology. In some embodiments, the {[S/T]-x-E-x-P} motif is also referred to as a conserved amino acid motif, conserved adherence motif, or CAMo-1. Binding of HMGB1 to this motif inactivates and down-regulates these virulence mechanisms as shown specifically through HMGB1 interaction with the target protein FimH in *E. coli*. Therefore, therapies and diagnostics tests related to microbial virulence have been developed using HMGB1.

Accordingly, provided herein are the HMGB1 polypeptides or fragments or mimetics thereof (e.g., SEQ ID NOs: 1, 2, or 3) for use in the therapeutic, screening, and diagnostic applications described herein. In some embodiments, fragments or variants or mimetics of HMGB1 that retain binding to microbial amino acid motifs and/or biological function are provided. In some embodiments, variants are at least 80% (e.g., at least 80%, 85%, 90%, 95%, 96%, 97%, 98%, or 99%) identical to wild type HMGB1 or the corresponding fragment thereof.

In some embodiments, HMGB1 peptides are provided. In some embodiments, peptides are at least 3 (e.g., at least 5, 10, 15, 20, 25, or more) amino acids in length.

Percent sequence identity can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

In some embodiments, 1, 2, 3, or 4 amino acids from the polypeptides or peptides described herein may be deleted. In some embodiments, 1, 2, 3, or 4 amino acids may be inserted into the peptides or added to either the C or N terminal end. In some embodiments, 1, 2, 3, or 4 amino acids within the polypeptides or peptides may be replaced with other amino acids. Suitable amino acid substitutions include conservative amino acid substitutions. For example, individual amino acid substitutions can be selected from any one of the following: 1) the set of amino acids with nonpolar side chains, for example, Ala, Cys, Ile, Leu, Met, Phe, Pro, Val; 2) the set of amino acids with negatively charged side chains, for example, Asp, Glu; 3) the set of amino acids with positively charged side chains, for example, Arg, His, Lys; and 4) the set of amino acids with uncharged polar sidechains, for example, Asn, Cys, Gln, Gly, His, Met, Phe, Ser, Thr, Trp, Tyr, to which are added Cys, Gly, Met and Phe.

A naturally occurring amino acid can also be replaced with, for example, a non-naturally occurring amino acid such as, for example, norleucine, ornithine, norvaline, homoserine, and other amino acid residue analogues such as those described in Ellman et al., Meth. Enzym., 1991, 202, 301-336. To generate such non-naturally occurring amino acid residues, the procedures of Noren et al., Science, 1989, 244, 182 and Ellman et al., supra, can be used. Other suitable methods are described in White et al., Methods, 2013, 60, 70-74; Gentilucci et al., Curr Pharm Des 2010, 16, 3195-3203; Hodgson & Sanderson, Chem Soc Rev 2004, 33, 422-430 and Krebs et al., Chemistry 2004, 10:544-553.

The polypeptides and peptides described herein can further be modified. Some modifications may increase the stability and activity of a peptide to enable reduced dosing level or frequency, as well as enable alternative routes of administration, e.g., oral or inhalation. The following are examples of modifications of peptides that may increase stability, activity, specificity, and/or efficacy.

1) Replace labile amino acids with ones that increase stability and improve activity. Such replacement can be performed based upon HPLC analysis of peptide incubation in serum or liver/lung homogenates. For example, lysines and arginines that are recognized by trypsin can be replaced with glutamine.

2) Replace one or more L-amino acids with D-amino acids. D-amino acids are unnatural amino acids which are less likely to be attacked by proteases. For example, a protease cleavage site prediction program has identified 8 cleavage sites for trypsin. To reduce the probability of this proteolysis, one or more L-arginines (R) in the peptide can be replaced with D-arginines as described by Powell et al. (Pharm. Res., 1993, 10, 1268-1273.)

3) Reduce the size of the peptide. Removing non-essential sequences or individual residues may improve entry into target cells. Use of smaller transduction domains, such as those described herein, may be carried out. An example of similar successful manipulation of somastatin is described in Harris (Gut, 1994, 35 (3 Suppl), 51-4).

4) Oligomerized peptide. If the peptide molecular weight is less than 5 kDa it is likely to be rapidly excreted through kidneys. Oligomerization may improve bioavailability. Oligomerization can be carried out by synthesizing repeating sequences such as dimers, trimers and polymers to increase the molecular mass so the peptide will be more stable and less easily excreted. These oligomers (n=number of repeats) may consist of repeats of the whole structure.

5) Cyclized peptide. Cyclizing a peptide may protect it against proteolysis and degradation. As described herein, cyclizing a peptide may occur via side-chain to side-chain. Further, cyclizing a peptide may occur through commonly used coupling methods using agents such as, for example, p-nitrophenyl esters, the azide method, 2,4,5-trichlorophenyl and pentafluorophenyl esters and the mixed anhydride method. Other more direct methods of activation using N,N-dicyclohexylcarbodiimide (DCC) with catalysts such as HOBt, HONSu, and HOAt are also suitable. Use of use of a water soluble carbodiimide EDC (1-ethyl-3-(3-dimethylaminopropyl)carbodiimide hydrochloride) is also suitable. Suitable successors to the conventional azide coupling includes the use of DPPA and PyBrop. Also included are: 1-benzotriazole-tris-dimethyl aminophosphonium hexafluorophosphate (BOP), O-(benzotriazol-1-yl)-1,1,3,3-tetramethyl uronium hexafluorophosphate (HBTU), 1-benzotriazolyloxy-tris-pyrrolidino-phosphonium hexafluorophosphate (PyBOP), O-(benzotriazol-1-yl)-1,1,3,3-tetramethyl uronium tetrafluoroborate (TBTU), 7-azabenzotriazol-1-yloxytrispyrrolidino phosphonium hexafluorophosphate (PyAOP), O-(7-azabenzotriazol yl)-1,1,3,3-tetramethyl uronium hexafluorophosphate (HATU), 7-azabenzotriazol-1-yloxy-tris-dimethyl aminophosphonium hexafluorophosphate (AOP), O-(7-azabenzotriazol-1-yl)-1,1,3,3-tetramethylene uronium hexafluorophosphate (HAPyU), and O-(7-azabenzotriazol yl)-1,1,3,3-pentamethylene uronium hexafluorophosphate (HAPipU). See, Davies, J. Peptide Science, 2003, 9, 471-501.

6) Internal hydrocarbon "stapling", that stabilizes peptide conformations. Examples of such methods are described by Bird et al., Methods Enzymol 2008, 446, 369-386; Madden et al., Chem Commun 2009, 37, 5588-5590; Kim et al., Org Lett 2010, 12, 3046-3049; Bird et al., PNAS 2010, 107, 14093-14098; Jacobsen et al., J Org Chem 2011, 76, 1228-1238 and Verdine & Hilinski, Methods Enzymol 2012, 503, 3-33.

7) PEGylation. Adding polyethylene glycol of different sizes, e.g., 40 kDa, to the amino-, carboxy-, and/or inside of the molecule may improve its stability. An example of the latter approach in stabilizing interferon alpha is described by Ramon et al. (Pharm. Res., 2005, 22, 1374-1386).

8) Other modifications: C-terminal amidation or N-terminal acetylation as described in, for example, Brinckerhoff et al. (Int'l J. Cancer, 1999, 83, 326-334), or N-pyroglutamylation as described in, for example, Green et al. (J. Endocrinol., 2004, 180, 379-388). Other examples include conjugation of various fatty acids ranging from 4-18 chain length as described in, for example, DasGupta et al. (Biol. Pharma. Bull., 2002, 25, 29-36).

9) Biodegradable modifications: e.g., polymers of N-acetylneuraminic adid (poysialic acids) as described in, for example, Georgiadis et al. (Cell. Mol. Life Sci., 2000, 57, 1964-1969).

10) Combination with delivery systems that enable sustained release or targeting to specific locations within the subject. Carriers such as liposomes, microspheres or microcapsules, poly lactic acid (PLA), poly lactic/glycolic acid (PLGA) as described in, for example, Heya et al. (J. Pharm. Sci., 1994, 83, 798-801), nanoparticles and emulsions, cyclodextrins and derivatives.

11) Formulations that protect peptides such as those containing different types of protease inhibitors. In addition, formulation containing multifunctional polymers which exhibit mucoadhesive properties as well as enzyme inhibitory activity, e.g., poly(acrylates), thiolated polymers, and polymer-enzyme inhibitor conjugates.

Other modifications may further include conjugation of the polypeptide, or a synthetically modified polypeptide, with a biologically active agent, label or diagnostic agent anywhere on the polypeptide scaffold, e.g., such as at the N-terminus of the polypeptide, the C-terminus of the polypeptide, on an amino acid side chain of the polypeptide, or another site. Such modification may be useful in delivery of the peptide or biologically active agent to a cell, tissue, or organ or identification in a screening assay. Such modifications may allow for targeting to a particular type of cell or tissue. Conjugation of an agent (e.g., a label, a diagnostic agent, a biologically active agent) to the inventive polypeptide may be achieved in a variety of different ways. The agent may be covalently conjugated, directly or indirectly, to the polypeptide at the N-terminus or the C-terminus of the polypeptide chain. Alternatively, the agent may be noncovalently conjugated, directly or indirectly, to the polypeptide at the N-terminus or the C-terminus of the polypeptide chain. Covalent conjugation is by means of one or more covalent bonds. Noncovalent conjugation is by means of one or more noncovalent bonds. Conjugation may also be via a combination of non-covalent and covalent forces/bonds. The agent may also be conjugated through a covalent or noncovalent linking group. Any number of covalent bonds may be used in the conjugation of a biologically active agent and/or diagnostic agent to the inventive polypeptide present invention. Such bonds include amide linkages, ester linkages, disulfide linkages, carbon-carbon bonds, carbamate, carbonate, urea, hydrazide, and the like. In some embodiments, the bond is cleavable under physiological conditions (e.g., enzymatically cleavable, cleavable with a high or low pH, with heat, light, ultrasound, x-ray, etc.). However, in some embodiments, the bond is not cleavable.

In some embodiments, peptidomimetics of the peptides described herein are provided. The use of peptides as lead compounds, and subsequently conversion into low-molecular-weight nonpeptide molecules (peptidomimetics), have successfully led to development of small-molecule antagonists of intracellular targets (Bottger et al., J. Mol. Biol., 1997, 269, 744-56; Bottger et al., Oncogene, 1996, 13, 2141-7). Therefore, peptidomimetics have emerged as a powerful means for overcoming the obstacles inherent in the physical characteristics of peptides, improving their therapeutic potential (Kieber-Emmons et al., Curr. Opin. Biotechnol., 1997, 8, 435-41; Beeley, Trends Biotechnol., 1994, 12, 213-6; and Moore et al., Trends Pharmacol. Sci., 1994, 15, 124-9). In some embodiments, compared to native peptides, peptidomimetics possess desirable pharmacodynamic properties superior to natural peptides, including good oral activity, long duration of action, better transport through cellular membranes, decreased rate of excretion, and decreased hydrolysis by peptidases.

Development of a small molecule peptidomimetic generally involves identification of the smallest functional peptide unit capable of inhibiting the targeted interaction. A growing body of literature demonstrates that high-affinity ligands can be selected from peptide libraries displayed on bacteriophage (Sulochana et al., Curr. Pharm. Des., 2007, 13, 2074-86; Cwirla et al., Proc. Natl. Acad. Sci. USA, 1990, 87, 6378-82; Scott et al., Science, 1990, 249, 386-90; and Devlin et al., Science, 1990, 249, 404-6), and many applications have been directed toward antagonizing the function of a protein ligand (Dower, Curr. Opin. Chem. Biol., 1998, 2, 328-34; and Sidhu et al., Methods Enzymol., 2000, 328, 333-63). Because the libraries can be very large ($10^{11}$ or more individual members), no initial assumptions are required concerning how to bias the library, nor the selective enrichment of rare binding phage through biological amplification and rescreening. Those sequences that bind can be identified easily by sequencing their encoding DNA.

In some embodiments, peptide ligands such identified further serve as starting points for a combinatorial chemistry approach or a medicinal chemistry-based peptidomimetic approach for the development of new directed therapeutic agents. In addition, the determination of the structural basis for the high-binding affinity of these peptides for their substrate contributes to the rational design of a therapeutic agent.

In some embodiments, peptides are synthesized de novo. A variety of peptide synthesis methods may be utilized. Examples include, but are not limited to, solid-phase peptide synthesis (SPPS), (R. B. Merrifield (1963). "Solid Phase Peptide Synthesis. I. The Synthesis of a Tetrapeptide". J. Am. Chem. Soc. 85 (14): 2149-2154; Mitchell, A. R. K., S. B. H.; Engelhard, M.; Merrifield, R. B. (1978). "A new synthetic route to tert-butyloxycarbonylaminoacyl-4-(oxymethyl)phenylacetamidomethyl-resin, an improved support for solid-phase peptide synthesis". J. Org. Chem. 43 (13): 2845-2852). Recent developments in synthesis methods are further described in Hojo, Curr Opin Struct Biol 2014, 26C, 16-23; Ramakers et al., Chem Soc Rev 2014, 43, 2743-2756 and Chandrudu et al., Molecules 2013, 18, 4373-4388.

In SPPS, small solid beads, insoluble yet porous, are treated with functional units ('linkers') on which peptide chains can be built. The peptide will remain covalently attached to the bead until cleaved from it by a reagent such as anhydrous hydrogen fluoride or trifluoroacetic acid. The peptide is thus 'immobilized' on the solid-phase and can be retained during a filtration process, whereas liquid-phase reagents and by-products of synthesis are flushed away.

The general principle of SPPS is one of repeated cycles of coupling-wash-deprotection-wash. The free N-terminal amine of a solid-phase attached peptide is coupled (see below) to a single N-protected amino acid unit. This unit is then deprotected, revealing a new N-terminal amine to which a further amino acid may be attached. The superiority of this technique partially lies in the ability to perform wash cycles after each reaction, removing excess reagent with all of the growing peptide of interest remaining covalently attached to the insoluble resin.

There are two majorly used forms of SPPS—Fmoc and Boc. Unlike ribosome protein synthesis, solid-phase peptide synthesis proceeds in a C-terminal to N-terminal fashion. The N-termini of amino acid monomers is protected by either of these two groups and added onto a deprotected amino acid chain.

In some embodiments, HMGB1 is produced by expressing a plasmid encoding HMGB1 polypeptide or a fragment thereof in a bacterial or eukaryotic expression vector. In some embodiments, the recombinant HMGB1 polypeptide or fragment thereof is fused to a tag to facilitate purification. The recombinant HMGB1 polypeptide or fragment thereof may be purified from cell-free production systems or from producing cells (bacteria, insect cells, or mammalian cells). In some embodiments, the HMGB1 polypeptide or fragment thereof is further purified or processed to reduce or remove any residual cellular components (e.g., toxins, lipopolysaccharides).

II. Therapeutic Applications

In some embodiments, the HMGB1 polypeptides or peptides, including variants thereof described herein, are used in the treatment of disease associated with (e.g., caused or exacerbated by) virulent microorganisms. For example, in some embodiments, the HMGB1 polypeptides are administered to a subject in need thereof in order to treat or prevent microbial virulence and associated disease. In some embodiments, the disease is an inflammatory or infectious disease (e.g., including but not limited to, inflammatory bowel disease, asthma (allergic and non-allergic) rheumatoid arthritis, non-alcoholic fatty liver disease, type II diabetes, urinary tract infections, pneumonia, and sepsis). In other embodiments, the disease may include certain types of cancer, such as, for example, carcinomas, chronic myelogenous leukemia (CML), breast cancers, and gastrointestinal cancers. Dysbiosis is another disease caused by microorganisms in which a microbial imbalance or maladaptation of microbes leads to intestinal and extra-intestinal disorders. Examples of infectious diseases include but not limited to gastrointestinal infections (cholera, salmonellosis, *Clostridium difficile* infections, listeriosis), sexually transmitted diseases (chlamydia, syphilis), meningococcal disease, dermatological infections (staphylococcal infections), lung infections (pertussis, pneumonia).

In some embodiments, HMGB1 polypeptides are conjugated to a therapeutic agent (e.g. antimicrobial agent, anti-inflammatory agent, or other agent). In some embodiments, HMGB1 polypeptides are administered in combination with a therapeutic agent (e.g., antimicrobial agent, anti-inflammatory agent, or other agent). In some embodiments, conjugation of modified HMGB1 to an antimicrobial drug is used to kill a specific subset of virulence-expressing microbes, potentially at doses low enough to spare non-targeted microbes.

Embodiments of the present invention further provide pharmaceutical compositions (e.g., comprising one or more of the therapeutic agents described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

In some embodiments, peptides described herein are introduced either subcutaneously or intravenously. In some embodiments, peptides are administered using a gene delivery technique to express the peptide in target (e.g., intestinal epithelial) cells. In some embodiments, recombinant adeno-associated virus (serotype 9) vectors carrying peptide-encoding cDNA with a cytomegalovirus promoter (AAV9) (Cutler M J, et al. Circulation. 2012; 126:2095-2104; herein incorporated by reference in its entirety) are utilized. In yet another embodiment, recombinant bacteria (e.g., *Lactobacillus*) carrying a gene encoding the peptide are utilized for expression of the peptide in a subject.

Pharmaceutical compositions and formulations for topical administration (e.g., to tissues, wounds, organs, etc) may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the active agents of the formulation.

Dosing is dependent on severity and responsiveness of the disease state or condition to be treated, with the course of treatment lasting from several days to several months, or until a cure is effected or a diminution of the disease state is achieved. In some embodiments, treatment is administered in one or more courses, where each course comprises one or more doses per day for several days (e.g., 1, 2, 3, 4, 5, 6) or weeks (e.g., 1, 2, or 3 weeks, etc.). In some embodiments, courses of treatment are administered sequentially (e.g., without a break between courses), while in other embodiments, a break of 1 or more days, weeks, or months is provided between courses. In some embodiments, treatment is provided on an ongoing or maintenance basis (e.g., multiple courses provided with or without breaks for an indefinite time period). Optimal dosing schedules can be calculated from measurements of drug accumulation in the body of the patient. The administering physician can readily determine optimum dosages, dosing methodologies and repetition rates.

In some embodiments, dosage is from 0.01 μg to 100 g per kg of body weight, and may be given once or more daily, weekly, monthly or yearly. The treating physician can estimate repetition rates for dosing based on measured residence times and concentrations of the drug in bodily fluids or tissues.

III. Diagnostic and Screening Applications

The HMGB1 polypeptides described herein find use in a variety of screening and diagnostic applications. In some embodiments, HMGB1 is contacted with a sample from a subject containing or suspected of containing microorganisms (e.g., stool, mucosal, blood or blood product, urine, etc.) and the level of binding of HMGB1 to microbes in the sample is assessed (e.g., using flow cytometry or an immunoassay such as ELISA). In some embodiments, magnetic particles coated with antibodies targeting HMGB1 are used to isolate, capture, or enrich for microbes that bind to HMGB1. For example, particles or beads coated with an anti-HMGB1 antibody may be used to capture HMGB1-targeted live microbes that express virulence proteins. In this manner, microbes may be enriched from low abundance samples or captured from samples with abundant microbes. Alternatively, an HMGB1 peptide, fragment, or mimetic can be bound to a matrix and used to capture microbes from blood collected from patients with suspected systemic microbial infections (i.e., sepsis). In another embodiment, an HMGB1 peptide, fragment, or mimetic may be used to isolate a specific subset of microbes expressing virulence proteins from stool samples containing a large number of microbes.

In yet another embodiment, HMGB1 may be labeled with a fluorophore or tag, which can then be used to label or tag a microbe protein to which an HMGB1 peptide, fragment, or mimetic binds (i.e., a microbe protein comprising a CAMo-1 motif). A labeled HMGB1 peptide, fragment, or mimetic also can be further labeled with a fluorophore to provide a readout.

In some embodiments, the assay is used to predict response to specific therapies. For example, in some embodiments, the assay is performed prior to treatment and is then repeated one or more times after or during treatment. In some embodiments, the level of HMGB1 binding is compared at different times during treatment and is used to make a decision to change, stop, or increase the level of treatment.

In some embodiments, the assay is used to identify deficiencies in endogenous HMGB1 function in patients. For example, bacteria recovered from a sample taken from a subject where HMGB1 normally labels bacteria (e.g., the gastrointestinal tract) displays a negative readout for endogenous HMGB1 labeling. Using the modified HMGB1 described herein, the same bacteria recovered from a sample taken from a subject displays a positive HMGB1 label readout ex vivo. This positive readout indicates failure of the endogenous HMGB1 function and the diagnosis is a component of the subject's disease process.

In some embodiments, HMGB1 binding bacteria are identified (e.g., using ribosomal 16S sequencing or other known methods to identification). This has the advantage of isolating and concentrating only the microbes of interest in a disease process. For example, this technique can be used to improve the performance of blood cultures for diagnosis of sepsis.

EXPERIMENTAL

The following examples are provided in order to demonstrate and further illustrate certain preferred embodiments and aspects of the present invention and are not to be construed as limiting the scope thereof.

Example 1

Figure 1C:
FIG. 1C is a graph showing results of ELISA for HMGB1 protein in mucus isolated from the colon.
Figure 1D:
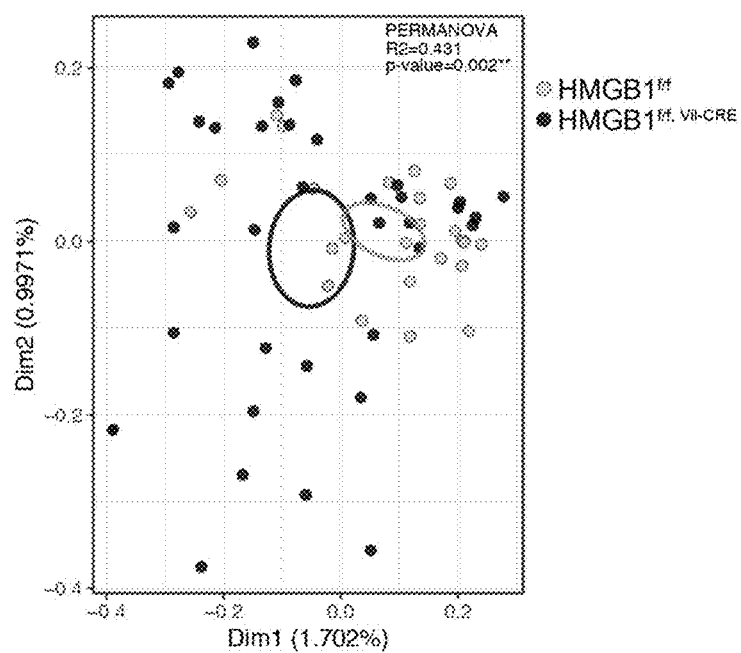
FIG. 1D is a PCoA plot of 16S rRNA sequences in mucosal scrapings from mice of the indicated genotypes. $R^2$ values reflect the influence of the genotype on the microbial community composition and indicate dysbiosis in the absence of HMGB1.

HMGB1 is active in gut antimicrobial defense. HMGB1 is found at high concentrations in the mucus layer overlying the colonic epithelial surface of wild type mice (HMGB1$^{f/f}$), but not mice conditionally deficient in IEC HMGB1 (HMGB1$^{f/f,\ Vil-CRE}$) (FIGS. 1A and 1B). Loss of IEC HMGB1 changes the microbial community composition, as assessed by 16S rRNA sequencing in mucosal scrapings (FIG. 1D). Fluorescence in situ hybridization (FISH) using eubacterial probes showed that bacteria in HMGB 1$^{f/f,\ Vil-CRE}$ mice are localized in close proximity to the epithelial surface with loss of the normal separation between host and microbe seen in HMGB 1$^{f/f}$ mice (FIGS. 1E and 1F). Enzyme-linked immunosorbent assay (ELISA) for HMGB1 protein in mucus isolated from the colon showed that HMGB1 produced by intestinal epithelial cells is found in colonic mucus (FIG. 1C). Quantitative PCR (q-PCR) for the 16S rRNA gene was performed using bacterial DNA isolated from a mucosal scraping of a 1 cm piece of colon and showed that there are more adherent bacteria in mice lacking HMGB1 in their intestinal epithelial cells (FIG. 1G). There are no significant differences in Muc1, Muc2, or Muc3 expression, the number of goblet cells, or autophagy in unchallenged HMGB1$^{f/f}$ and HMGB1$^{f/f,\ Vil-CRE}$ mice. This shows that differences in mucus production or release are not responsible for the differences in bacterial localization within the colon. Immunofluorescence of Carnoy's-fixed colons from HMGB1$^{f/f}$ (FIG. 1H) and HMGB1$^{f/f,\ Vil-CRE}$ mice (FIG. 1O stained with an anti-fungal antibody that broadly recognizes commensal fungi found in the gut showed that HMGB1 deficient mice have increased numbers of fungi and the fungi are found in close proximity to the mucosal surface.

Taken together these data identify HMGB1 as a key protein in colonic antibacterial and antifungal defense under physiologic conditions and indicate that this function plays a major role in IBD pathophysiology. This is a completely unexpected function for this protein and represents major paradigm shifts in the gastrointestinal physiology and HMGB1 biology fields. It also provides a unique opportunity to use this interaction to identify and monitor disease-causing bacteria and fungi in the gut.

Example 2

This example demonstrates that HMGB1 targets a specific amino acid motif (CAMo-1) in microbial virulence proteins to inactivate them.

E. coli FimH is an HMGB1 target protein. The HMGB1 interaction motif, CAMo-1, is composed of conserved and variable (X) amino acids (FIG. 2A). The CAMo-1 motif was previously identified in mammalian proteins and was found in a number of microbial motility and adhesion proteins, including FimH of E. coli (FIG. 2B). FimH sits at the tip of type I fimbrae and mediates attachment of a number of bacteria, including E. coli, to mammalian cells (10). Both E. coli and the FimH gene have been implicated in IBD since patients with both CD and UC have increased association of E. coli with the mucosal surface of the gut epithelium and mutations in the FimH gene have been reported in IBD-associated E. coli (8,9). The red blood cell (RBC) agglutination assay is a proxy for epithelial attachment since the bacteria attach to mannose on the RBC, the same substance that they attach to on epithelial cells (24). In this assay bacteria attach to and cross-link RBC leading to a hazy, mat-like appearance in wells. Inhibition of agglutination allows the RBC to accumulate at the bottom of the well leading to the appearance of a dot in the well. Despite a previous report that HMGB1 kills microbes, no decreased viability was observed in E. coli (25). Thus, HMGB1 directly inhibits microbial virulence mechanisms that are particularly relevant for the pathophysiology of IBD. HMGB1 interacts with FimH on the surface of E. coli and prevents their adherence to mammalian cells (FIGS. 2C and 2D).

Figure 2H:
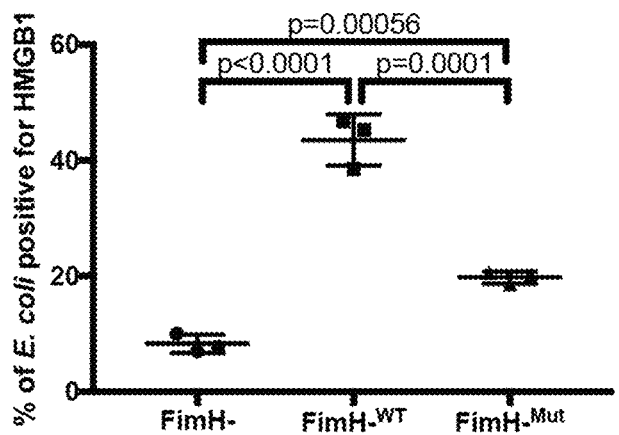
FIGS. 2H and 2I are graphs showing the results of flow cytometry of E. coli deficient in FimH (FimH-) or FimH- E. coli complemented with plasmids containing wild type FimH (FimH-$^{WT}$) or FimH mutated in the conserved amino acids of CAMo-1 (FimH-$^{Mut}$). Mutation of CAMo-1 significantly decreased HMGB1 binding to E. coli. Both the number of positive bacteria (FIG. 2H) and the amount of HMGB1 deposited on each bacterium (FIG. 2I) were decreased.
Figure 2I:
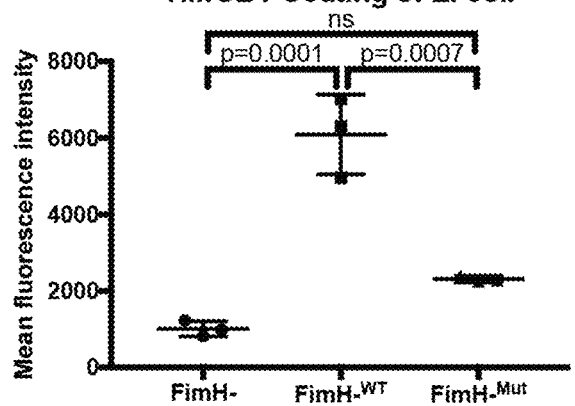
Figure 2J:
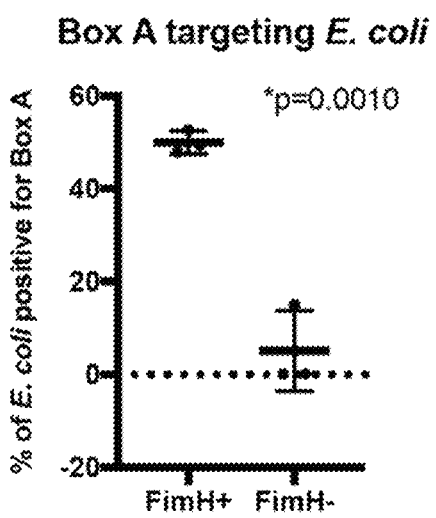
FIGS. 2J and 2K are graphs showing results of flow cytometry on wild type (FimH+) or FimH knockout (FimH-) E. coli treated with Box A protein and stained with anti-HIS antibody.
Figure 2K:
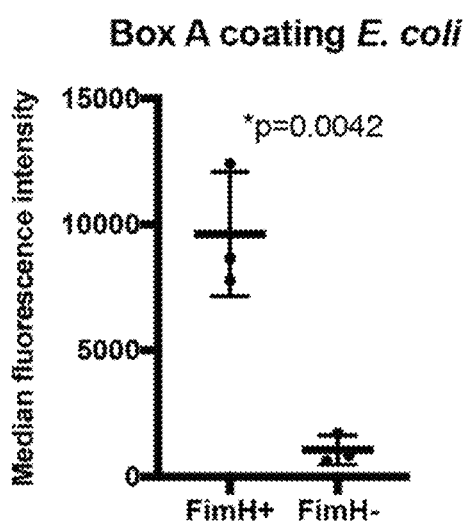

CaCo2 cells (human intestinal epithelial cell line) were exposed to wild type untreated E. coli (K12) or E. coli treated with recombinant human HMGB1 produced in mammalian cells. Exposure to HMGB1 significantly reduced the number of adherent bacteria (see FIGS. 2E-2G). Flow cytometry was performed with E. coli deficient in FimH (FimH-) or FimH- E. coli complemented with plasmids containing wild type FimH (FimH-WT) or FimH mutated in the conserved amino acids of CAMo-1 (FimH-Mut). As shown in FIGS. 2H and 2I, mutation of CAMo-1 significantly decreased HMGB1 binding to E. coli. Both the number of positive bacteria and the amount of HMGB1 deposited on each bacterium were decreased. In addition, flow cytometry of wild type (FimH+) or FimH knockout (FimH-) E. coli (K12) treated with Box A protein and stained with anti-HIS antibody showed that Box A specifically labels bacteria expressing the virulence protein FimH (FIGS. 2J and 2K).

Example 3

This example demonstrates that decreased localization of HMGB1 protein to the surface of the colon is associated with increased numbers of adherent bacteria and fungi in inflammatory bowel disease patients.

Figure 6F:
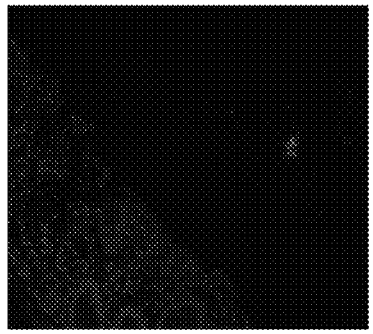
FIGS. 6F-6H show immunofluorescent microscopy of fungal staining in sections of resected colon from non-IBD (FIG. 6F), ulcerative colitis (FIG. 6G), and Crohn's disease (FIG. 6H) patients.
Figure 6G:
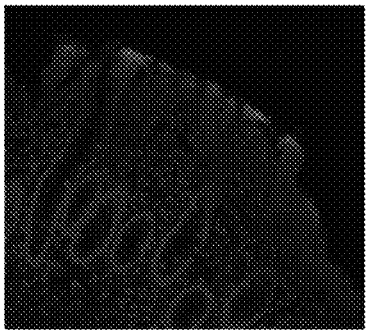
Figure 6H:
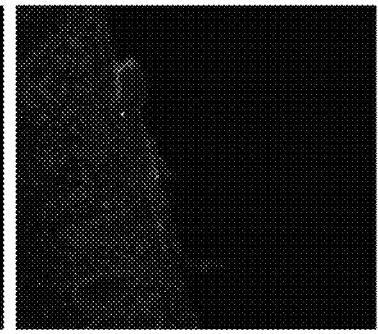
Figure 7:
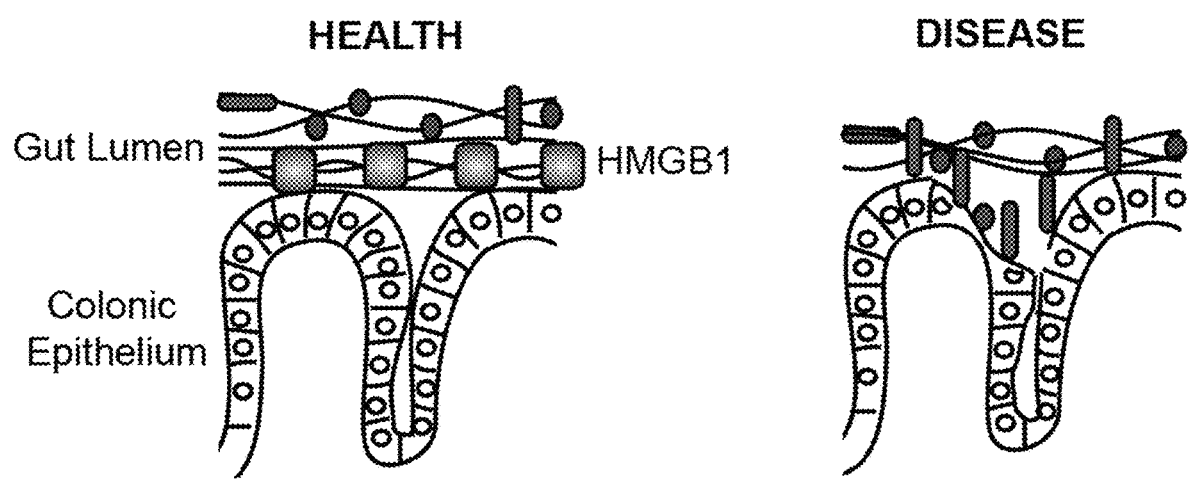
FIG. 7 is a model figure showing the role of HMGB1 at the surface of the intestine in health and how microbes come into contact with the surface of the intestine and cause damage to the tissues when HMGB1 is absent from the surface of the intestine.

Immunofluorescence microscopy showed that HMGB1 is abundant in the mucus layer from the healthy gut (FIG. 6A) and only present in a small amount in the diseased gut (FIG. 6B). FimH expression is only appreciated in the diseased gut. Immunofluorescence microscopy of sections of resected colon from non-IBD (FIG. 6C), ulcerative colitis (FIG. 6D), and Crohn's disease (FIG. 6E) patients showed that, as in mice, HMGB1 forms a layer in the mucus overlying the surface of the colon. Immunofluorescence microscopy of resected colon shows fungal staining from sections of non-IBD (FIG. 6F), ulcerative colitis (FIG. 6G), and Crohn's disease (FIG. 6H) patients.

Example 4

This example demonstrates that HMGB1 targeting also suppresses bacterial expression of E. coli FimH.

Figure 3A:
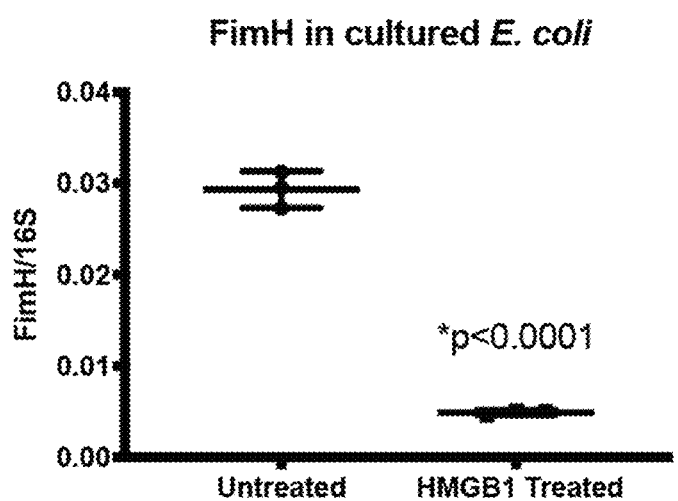
FIG. 3A is a graph showing the results of qRT-PCR for FimH gene expression in E. coli (K12) treated with 3 µM HMGB1 for 2 hours. Exposure to HMGB1 in vitro decreased expression of FimH.
Figure 3B:
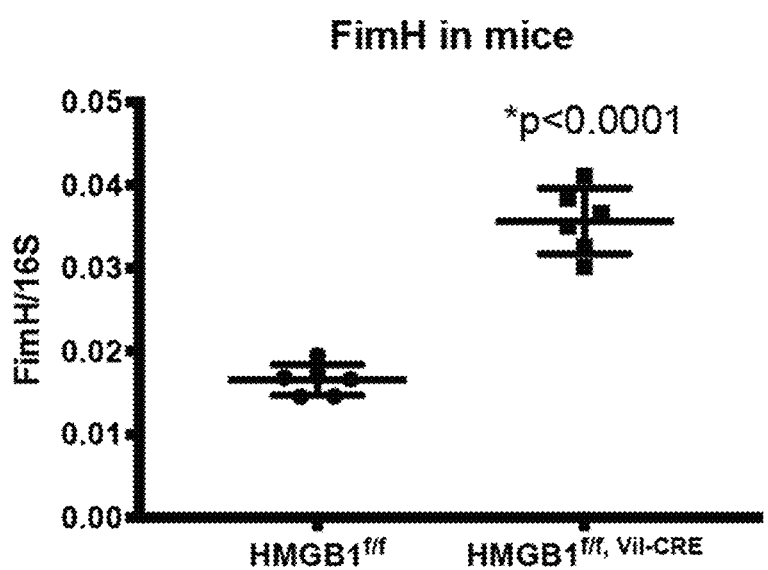
FIG. 3B is a graph showing results of qRT-PCR for E. coli FimH gene expression in mucosal scrapings from HMGB1$^{f/f}$ and HMGB1$^{f/f\ Vil-CRE}$ mice. Exposure to HMGB1 in vivo decreased expression of FimH.
Figure 3C:
FIG. 3C is an image of immunoblotting for FimH in mucosal scrapings from HMGB1$^{f/f}$ and HMGB1$^{f/f;\ Vil\text{-}CRE}$ mice.
Figure 4A:
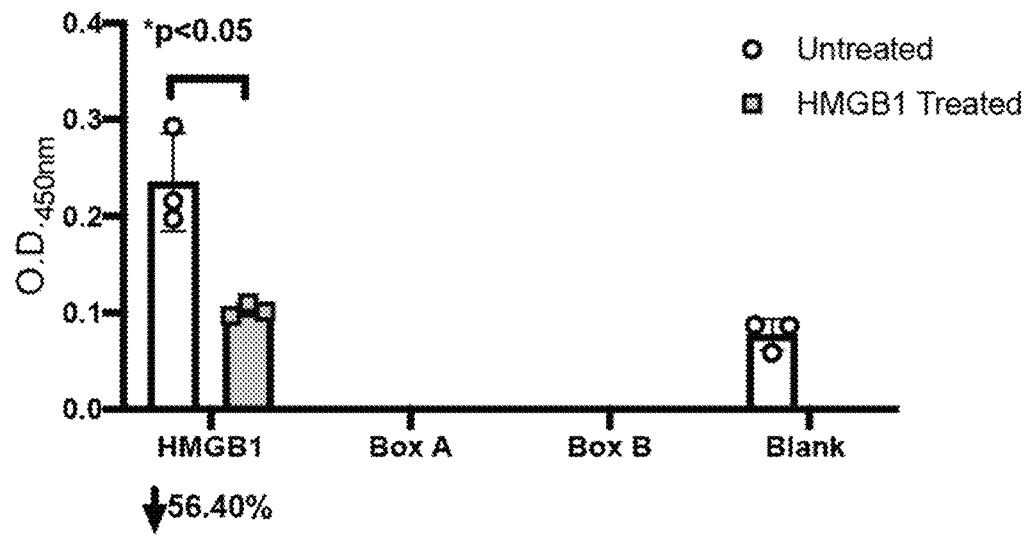
FIGS. 4A-4D are graphs illustrating that HMGB1 and a truncation mutant composed of aa 2-97 of HMGB1 (Box A) are able to disrupt adhesin-ligand interactions that are required for microbial adherence and disease.
Figure 4B:
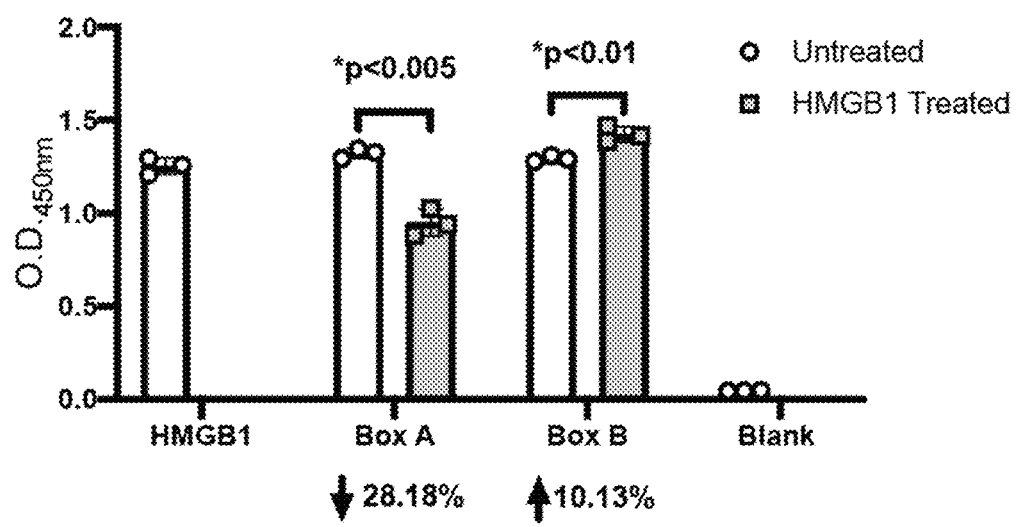
Figure 4C:
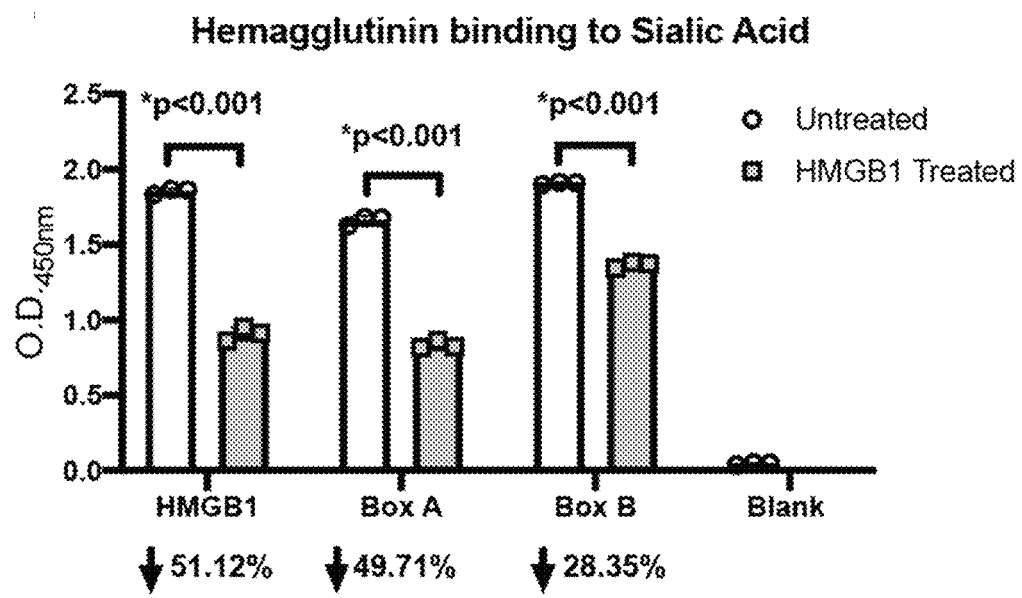
Figure 4D:
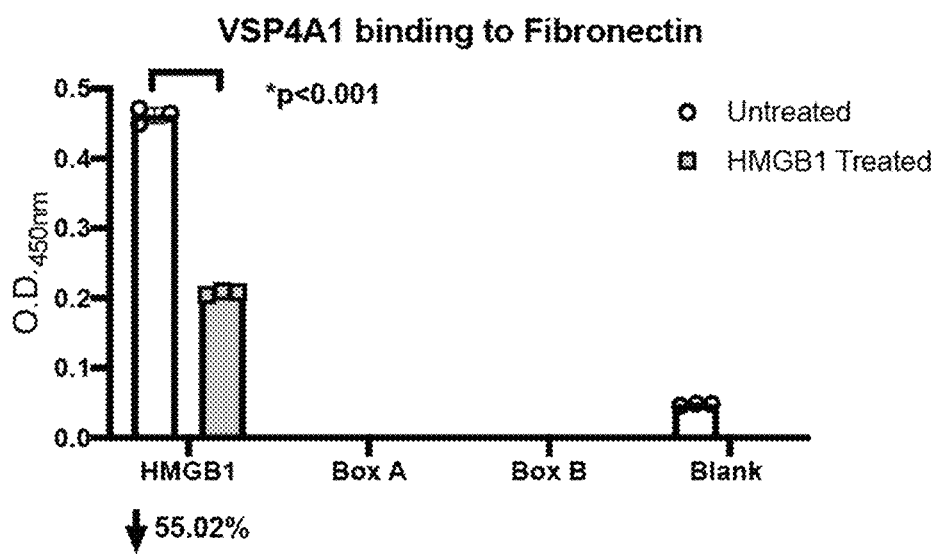

Quantitative reverse transcriptase (qRT-PCR) for FimH gene expression was performed in E. coli (K12) treated with 3 μM HMGB1 for 2 hours. Exposure to HMGB1 in vitro decreased expression of FimH, as shown in FIG. 3A. qRT-PCR for E. coli FimH gene expression also was performed in mucosal scrapings from HMGB1$^{f/f}$ and HMGB1$^{f/f,\ Vil\text{-}CRE}$ mice. Exposure to HMGB1 in vivo decreased expression of FimH, as shown in FIG. 3B. Immunoblotting for FimH in mucosal scrapings from HMGB1$^{f/f}$ and HMGB1$^{f/f,\ Vil\text{-}CRE}$ mice showed that exposure to HMGB1 in vivo also decreased levels of FimH protein, as shown in FIG. 3C.

Example 5

This example demonstrates that HMGB1 and HMGB1 derivatives are able to disrupt microbial adhesin-ligand interactions required for adherence to host tissues.

Adhesins bind to carbohydrates on host cells or extracellular matrix components to anchor microbes in place. Since this is the first and most vital step for microbe-related disease, disrupting the interaction between an adhesin and its target ligand is considered to be protective against disease. HMGB1 or Box A from HMGB1 can disrupt adhesin-ligand interactions using the adhesins FimH from *E. coli* (Gm− bacterium), Asa 1 from *Enterococcus faecalis* (Gm+ bacterium), Hemagglutinin from Influenza B (virus), and VSP4A1 from *Giardia intestinalis* (protozoan), as shown in FIGS. 4A-4D.

Collectively, these data demonstrate that HMGB1 can disrupt adhesion events that are critical for microbial binding to host tissues or cells from Gm− bacteria, Gm+ bacteria, viruses, and protozoa. Since fungal adhesins also bind to carbohydrate ligands on host cells and contain CAMo-1, HMGB1 most likely broadly targets adhesins from bacteria, viruses, fungi, and protozoa. Furthermore, Box A of HMGB1 recapitulates the functions of the full-length protein.

Example 6

This example demonstrates that HMGB1 interaction with microbes can be used to isolate, identify, and/or capture those microbes expressing virulence factors.

Figure 5:
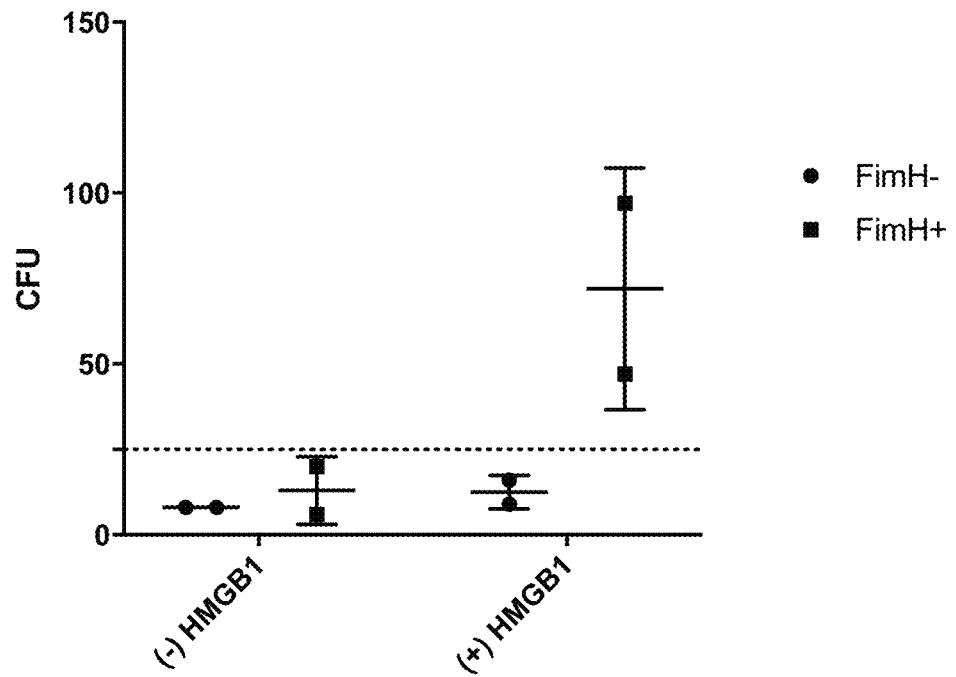
FIG. 5 is a graph showing isolation of *E. coli* treated with full-length HMGB1 protein using anti-HMGB1 antibody-coated beads.

HMGB1 or Box A selectively binds only to microbes expressing virulence proteins. This binding can be used to identify, capture, and isolate microbes expressing virulence proteins containing CAMo-1. Cultured *E. coli* positive or negative for the virulence factor FimH were treated with recombinant HMGB1 and the live bacteria were immunoprecipitated with anti-HMGB1 antibody and magnetic beads. The number of recovered bacteria were then plated, cultured overnight, and the colony-forming units were counted (FIG. 5). Therefore, HMGB1 specifically interacts with bacteria expressing microbial virulence characteristics and can be used to identify, isolate, and monitor those bacteria.

Example 7

Experiments will be conducted to identify disease causative bacteria and develop a biomarker to monitor them by 1) using host innate immune detection to identify bacteria that are putative agents of disease in inflammatory bowel disease, 2) using species-appropriate model systems to interrogate mechanisms whereby these microbes contribute to IBD, and 3) evaluating HMGB1 labeling of gut bacteria as a marker of the microbial component of IBD.

It was shown that HMGB1 is found in colonic mucus where it acts to keep microbes separate from the intestinal epithelium. HMGB1 expression is significantly decreased in patients with active IBD, indicating that their HMGB1-mediated anti-microbial defenses are compromised. The specific mechanism of this defense is that HMGB1 binds to virulence factors expressed by normally commensal bacteria to inactivate those virulence mechanisms. The interaction between HMGB1 and bacterial proteins containing the HMGB1-interaction motif is sufficient for immunoprecipitation of whole bacteria. Using this interaction, HMGB1 of the invention is used to capture, identify, and characterize disease-causing bacteria in IBD patients. Immunoprecipitation using magnetic particles coated with antibodies targeting HMGB1 can be used to capture gut bacteria targeted by this innate immune defense system in health and disease.

Three model systems are used to develop a method to isolate and identify virulent bacteria in the gut: 1) Model microbial organisms (i.e. *E. coli*) cultured in vitro, 2) a murine model system, and 3) patient samples. *E. coli* is used as a model organism in these studies since it is a common gut commensal organism with the potential for virulence, it expresses FimH protein that contains the HMGB1 interaction motif, and it is thoroughly characterized and highly amenable to laboratory studies. *E. coli* strains that do or do not express FimH are used in these studies. *E. coli* K12 wild-type (FimH+) and FimH knockout (FimH-) bacteria will be obtained from the Keio collection housed at the *Coli* Genetic Stock Center and are grown under conditions designed to induce fimbrae expression. *E. coli* that are phase locked to always (FimON) or never express fimbrial genes (FimOFF) will be obtained from the Mobley Lab at the University of Michigan.

Wild type (HMGB1$^{f/f}$) mice and mice conditionally deficient in intestinal epithelial cell HMGB1 (HMGB1$^{f/f,\ Vil\text{-}CRE}$) will be used as the murine model system. All murine in vivo studies utilize 6-9 week-old age and sex-matched littermates of both sexes who are fed a standard laboratory chow diet and kept under standard light/dark conditions. In the studies of specific pathogen free (SPF) mice, the mice are exposed to mixed soiled bedding of both genotypes to normalize gastrointestinal bacterial communities for one week and then separated into cages based on their genotype. The mice are group housed as appropriate with a minimum of three separate cages for each genotype to minimize cage specific effects. Samples from healthy humans and patients with inflammatory bowel diseases are also used in these studies.

Antibodies and recombinant proteins are generated to optimize bead capture of bacteria that express microbial virulence in vitro using *E. coli* that do or do not express FimH and in vivo using samples of stool and mucosal scrapings from HMGB1$^{f/f}$ and HMGB1$^{f/f,\ Vil\text{-}CRE}$ mice. The in vitro studies are performed first and focus on a single organism, the in vivo studies utilize complex microbial communities isolated from mice. Captured bacteria are then subjected to downstream analysis for 16s ribosomal RNA gene sequencing, bacterial metagenomics, isolation and storage for future phenotyping assays, and ELISA for FimH expression. This assay is then performed on bacteria isolated from stool or the mucosal surface of biopsies from healthy patients or patients with IBD undergoing screening colonoscopy (healthy) or colonoscopy for disease management (IBD). Captured bacteria are analyzed as described previously. Normal patients are sampled at one time point. Each IBD patient is sampled at two time points at least 4 weeks apart during the study to allow analysis of the relationship between the HMGB1-targeted bacterial population and disease activity within and between patients. Disease activity is analyzed using standard clinical measures, including histological scoring, by the attending clinician. Bacterial samples from patients are treated ex vivo with recombinant HMGB1 to identify any microbes that were susceptible to targeting, but were not targeted due to failure of host antimicrobial defenses. These microbes are analyzed separately using the previously described methods.

The consequences of failed HMGB1 targeting of bacteria for mucosal inflammation and damage will be determined. As discussed herein, HMGB1 preferentially targets bacteria expressing FimH, a virulence factor that that has been implicated in IBD. FimH mediates bacterial adherence to intestinal epithelial cells, leading to inflammation and cell damage. HMGB1 targets FimH through a specific amino acid motif and this interaction causes bacteria to downregulate this virulence mechanism. The HMGB1 interaction motif is found in many microbial virulence proteins, suggesting that this is a mechanism to maintain microbes in commensal states and that when it fails, gut bacteria express virulence leading to epithelial damage and mucosal disease. The inflammatory response to virulence-expressing microbes is modified by their interaction with HMGB1. HMGB1 targeting represses expression of bacterial characteristics that trigger inflammation and cell damage in the intestinal epithelium.

Patient-derived organoids are grown as polarized monolayers in transwells. The apical surface of the organoids is treated with HMGB1 positive and negative bacteria from healthy individuals and IBD patients, and HMGB1 negative bacteria are treated ex vivo with recombinant HMGB1. Bacteria recovered without culturing are used in order to preserve the context of the host in the bacteria. If sufficient biomass is not available, then short-term cultures of the microbes are performed using standard culture media under anaerobic conditions. Samples are then tested for Interleukin-8 production by ELISA as a measure of inflammation in response to the bacteria. Immunoblotting for activated caspase-3 is performed to determine whether exposure to disease-associated bacteria kills IEC and whether that killing is modified by HMGB1 targeting. It will be determined whether HMGB1-mediated gut antimicrobial defense failure in IBD is due to (a) loss of HMGB1 expression, (b) loss of HMGB1 localization, (c) acquisition of a microbe that cannot be targeted by HMGB1, (d) inappropriate targeting that leads to loss of beneficial microbial functions, or (e) loss of microbial feedback mechanisms that regulate virulence factor expression after HMGB1 targeting.

HMGB1 bacterial targeting will be utilized to develop a biomarker for the microbial component of IBD. There are currently very few biomarkers of IBD disease severity and all are focused on the host component of disease. Despite the current consensus that bacteria are a major contributor to IBD pathophysiology, there is currently no method to identify or quantify the microbial contribution to these diseases. The finding that HMGB1 targets bacteria expressing virulence characteristics and that HMGB1 expression is decreased in IBD indicates that HMGB1 targeting of bacteria is useful as a biomarker for the microbial component of IBD.

HMGB1-mediated bacterial targeting is quantified to develop an Assessment of Disease in Microbes (ADiM) Index during IBD. Initial studies are performed using HMGB1$^{f/f}$ and HMGB 1$^{f/f,\ Vil-CRE}$ mice and $E.\ coli$ to optimize an assay to quantify HMGB1 targeting and FimH expression in bacteria. In this assay, cultured FimH expressing or non-expressing $E.\ coli$ treated with recombinant HMGB1 are used. Complex microbial communities are isolated from mouse stool that are targeted in vivo by HMGB1 (microbes from HMGB1$^{f/f}$ mice) or targeted ex vivo with recombinant HMGB1 (microbes from HMGB1$^{f/f,\ Vil-CRE\ mice}$). The percentage and quantity of HMGB1 targeting and the relationship between HMGB1 targeting and FimH expression are quantified by flow cytometry and ELISA. Stool or mucosal biopsies from healthy and IBD patients are used to perform flow cytometry to identify the percentage of HMGB1 positive and HMGB1 negative microbes and quantify the amount of HMGB1 present on individual microbes. The microbes are treated with exogenous HMGB1 and flow cytometry is performed to identify the untargeted, but targeting eligible population of microbes. HMGB1 and FimH ELISAs are performed on bacteria isolated from healthy and IBD patients to corroborate the flow cytometry findings and evaluate a second method for quantifying HMGB1 targeting of potentially virulent microbes. These findings are used to create the ADiM index. This procedure is performed at one time point in healthy patients and two different time periods in each IBD patient and the ADiM index is evaluated with respect to disease severity, response to therapy, and its ability to predict clinical outcomes. The difference between targeted and untargeted, but targeting eligible microbes is expected to be the major indicator of microbial disease in IBD patients. The amount of HMGB1 deposited on bacteria is also quantified and used as a measure of microbial disease in IBD patients.

Example 8

This example describes methods to determine the mechanisms of HMGB1-mediated gut antibacterial defense and the mechanisms leading to the presence of HMGB1 in colonic mucus.

Antimicrobial immune effectors, such as antimicrobial peptides, mucus, and secretory IgA, are produced and released into the gut in response to microbes, and subsequently affect the types of bacteria that colonize the gut and their physical location within the intestinal lumen (16). Data demonstrate that HMGB1 is found in colonic mucus under physiologic conditions, its absence leads to changes in the localization of gut microbes, and its expression is increased in response to the bacterial component muramyl dipeptide (21). These factors demonstrate that HMGB1 is a novel antimicrobial defense protein that is produced in IEC in response to bacteria and then released into colonic mucus.

All murine in vivo studies will utilize 6-9 week old age and sex-matched littermates of both sexes who are fed a standard laboratory chow diet and kept under standard light/dark conditions. The germ free (GF) mice are housed in the Gnotobiotic Core Facility of the University of Chicago Digestive Disease Research Core Center (DDRCC). These mice were originally derived germ-free by Taconic Laboratories. In the studies of SPF mice, the mice are exposed to mixed soiled bedding of both genotypes to normalize gastrointestinal bacterial communities for one week and then separated into cages based on their genotype. The mice are group housed as appropriate with a minimum of three separate cages for each genotype to minimize cage-specific effects. After two weeks, the mice are sacrificed and their tissues used in the assay. Germ-free mice that are gavaged with live microbes (conventionalized) are maintained for 4 weeks to allow for immune system development, and then sacrificed. Conventionalized mice are kept in bacterial isolators to prevent additional colonization by microbes from the environment and colonization efficiency is evaluated by culture and counting colony forming units (cfu) of bacteria recovered from stool.

Colonoids are prepared from mouse colons and cultured according to procedures well-known in the art and adapted by the Tissue Engineering and Cell Models Core of the University of Chicago P30 DDRCC. Colonoids are grown as 2D monolayers to allow cells to polarize for treatment of the apical surface with bacteria or bacteria-derived components and collection of samples of secreted products from the apical or basolateral compartments.

E. coli is used as a model organism in these studies since it is a common gut commensal organism with the potential for virulence, it expresses FimH protein that contains the HMGB1 interaction motif, and it is thoroughly characterized and highly amenable to laboratory studies. The E. coli K12 wild-type (FimH+) and FimH knockout (FimH-) will be obtained from the Keio collection housed at the Coli Genetic Stock Center and are grown under conditions designed to induce fimbrae expression. The Fim ON and Fim OFF strains will be obtained from the Mobley Laboratory at the University of Michigan. E. coli K12 is a well characterized laboratory strain that is not considered pathogenic; however, it is highly possible that it could have pathogenic effects in the absence of HMGB1. E. coli K12 expresses FimH and produces type I fimbria to attach to mammalian cells. FimH is a well-characterized TLR4 ligand and TLR4 stimulation is thought to lead to HMGB1 production (26). Recombinant FimH produced in E. coli, HMGB1 produced in mammalian cells, and peptides derived from HMGB1 will be purchased from commercial sources. Techniques for detecting HMGB1 are described herein (e.g., flow cytometry, microscopy, or ELISA).

Example 9

This example describes methods to determine the mechanisms whereby HMGB1 influences bacterial colonization or virulence.

Bacterial colonization of the gut requires the ability to transit to and establish residency within a replication permissible niche within the intestine. An essential aspect of colonization is avoidance of host defenses that kill bacteria or prevent them from attaching to host tissues or mucus that hold them within a niche. HMGB1 directly interacts with a bacterial protein known to be important for tissue adherence, and loss of HMGB1 in the gut lumen increases the physical proximity of bacteria to the intestinal epithelium.

Previous studies identified decreased HMGB1 protein levels in tissues from active IBD lesions regardless of location in the intestine (ileum or colon) or type of IBD (Crohn's disease or ulcerative colitis). Patients with both Crohn's disease and ulcerative colitis are used, focusing on tissues from the colon due to the high levels of bacteria and suspected relative importance of host antimicrobial defenses.

Bacteria are imaged in situ using Carnoy's fixed samples to preserve mucus or isolated from the mucosal-associated compartment of the colon by washing and gentle scraping for further assays. If recovery of bacteria from mice is too low for subsequent assays, samples from multiple mice are pooled or fecal lysates are used as the source of bacteria. If bacterial recovery from human biopsies is insufficient for downstream applications, samples using endoscopic brushing are used instead. Illumina Next Generation Sequencing and 16S rRNA taxonomic and metagenomic data from the gut microbial communities in mice and humans are obtained. Bioinformatic approaches are used to identify the types of bacteria targeted by HMGB1 as well as specific bacterial genes that are associated with HMGB1 targeting. Traditional microbial characterization of HMGB1-mediated regulation of E. coli are performed.

Initial data indicate that HMGB1 regulates the interaction between Gm negative bacteria (e.g., E. coli) and the colonic epithelium as well as Gm positive bacteria and fungi.

Example 10

This example describes methods to determine the mechanisms whereby HMGB1 regulates expression of bacterial characteristics associated with colonization and virulence.

Commensal characteristics are those aspects of bacteria normally present in the gut that are associated with colonization, but not damage to host tissues. When microbes shift from commensal to pathogenic behavior, this often involves increased expression of motility and adherence genes, which bring the bacteria in close contact with the host epithelium (29,30). HMGB1 in colonic mucus binds to motility and adhesion proteins on the cell surface of bacteria to prevent their intimate interaction with host epithelial tissues.

Cells that do or do not express HMGB1 may contribute a different set of host proteins to the mucus or supernatants or have different surface characteristics in addition to a difference in HMGB1 expression. These differences are biologically relevant since IBD patients have decreased levels of HMGB1 in their IEC. Direct effects of HMGB1 are examined using extracellular sources of HMGB1, HMGB1$^{f/f}$ colonoids, and HMGB1$^{f/f}$ colonoids. Effects measured included HMGB1 regulation of bacterial virulence characteristics (e.g., commensal, pathogenic, opportunistic), bacterial interaction with IEC in the presence of absence of extracellular HMGB1, and microbial colonization and virulence through changes to mucus production or release. Data showed that the change in microbial localization within the colonic mucus is most likely due to changes in motility and adhesion by gut microbes rather than changes to mucus production or release.

Example 11

This example describes the mechanisms underlying the role of HMGB1 in mitigating mucosal damage in the gut.

Loss of the physical separation between host cells and gut microbes is known to contribute to inflammation and damage in IEC (16). Data showed that HMGB1 binds to E. coli FimH and prevents bacterial adherence to mammalian cells. Measures of bacterial adherence and inflammation were established in mouse colonoids grown in 2D monolayers as previously described. HMGB1 exhibited direct effects to limit bacterial interaction with the epithelial surface and so limit microbe-induced stress, inflammation, and death in IEC.

Data demonstrated that HMGB 1$^{f/f, \; Vil-CRE}$ mice are more susceptible to colitis than wild-type mice, but only when they are challenged with dextran sodium sulfate (DSS) or IL-10 deficiency (21). The data presented herein shows that gut bacteria are found in close proximity to the epithelial surface in HMGB 1$^{f/f, \; Vil-CRE}$ mice. In addition, the proximity of the bacteria to the colonic epithelium imparts susceptibility to colitis, but isn't sufficient to induce disease on its own. This concept is in keeping with current paradigms of IBD pathophysiology. The proximity of bacteria to the epithelium likely changes inflammatory responses to the microbes, which primes the cells for death if counter-regulatory mechanisms fail, or if the stimuli change to hit an already active response for a second time. Therefore, HMGB1 in the gut lumen selects against microbes that contribute to colitis through triggering inflammation, IEC death, and mucosal damage.

REFERENCES

The following references are herein incorporated by reference in their entireties.
1. Sartor R B, Mazmanian S K. Intestinal Microbes in Inflammatory Bowel Diseases. Am J Gastroenterol Suppl. 2012; 1(1):15-21. doi:10.1038/ajgsup.2012.4.
2. Dalal S R, Chang E B. The microbial basis of inflammatory bowel diseases. J Clin Invest. 2014; 124(10):4190-4196. doi:10.1172/JCI72330.
3. Strober W, Darfeuille-Michaud A, Barnich N, et al. Adherent-invasive *E. coli* in Crohn disease: bacterial "agent provocateur". J Clin Invest. 2011; 121(3):841-844. doi:10.1172/JCI46333.
4. Chassaing B, Rolhion N, Vallee A de, et al. Crohn disease—associated adherent-invasive *E. coli* bacteria target mouse and human Peyer's patches via long polar fimbriae. J Clin Invest. 2011; 121(3):966-975. doi:10.1172/JCI44632.
5. Glasser A-L, Boudeau J, Barnich N, Perruchot M-H, Colombel J-F, Darfeuille-Michaud A. Adherent Invasive *Escherichia coli* Strains from Patients with Crohn's Disease Survive and Replicate within Macrophages without Inducing Host Cell Death. Infect Immun. 2001; 69(9):5529-5537. doi:10.1128/IAI.69.9.5529-5537.2001.
6. Agus A, Massier S, Darfeuille-Michaud A, Billard E, Barnich N. Understanding host-adherent-invasive *Escherichia coli* interaction in Crohn's disease: opening up new therapeutic strategies. Biomed Res Int. 2014; 2014:567929. doi:10.1155/2014/567929.
7. Small C-LN, Reid-Yu S A, McPhee J B, et al. Persistent infection with Crohn's disease-associated adherent-invasive *Escherichia coli* leads to chronic inflammation and intestinal fibrosis. Nat Commun. 2013; 4:346-361. doi:10.1038/ncomms2957.
8. Dreux N, Denizot J, Martinez-Medina M, et al. Point mutations in FimH adhesin of Crohn's disease-associated adherent-invasive *Escherichia coli* enhance intestinal inflammatory response. PLoS Pathog. 2013; 9 (1):e1003141. doi:10.1371/journal.ppat.1003141.
9. Rhodes J M. The role of *Escherichia coli* in inflammatory bowel disease. Gut. 2007; 56(5):610-612. doi:10.1136/gut.2006.111872.
10. Klemm P, Schembri M. Type 1 Fimbriae, Curli, and Antigen 43: Adhesion, Colonization, and Biofilm Formation. EcoSal Plus. 2004; 1 (1). doi:10.1128/ecosalplus.8.3.2.6.
11. Pratt L A, Kolter R. Genetic analysis of *Escherichia coli* biofilm formation: roles of flagella, motility, chemotaxis and type I pili. Mol Microbiol. 1998; 30(2):285-293.
12. Ha C W Y, Lam Y Y, Holmes A J. Mechanistic links between gut microbial community dynamics, microbial functions and metabolic health. World J Gastroenterol. 2014; 20(44):16498-16517. doi:10.3748/wjg.v20.i44.16498.
13. Morgan X C, Segata N, Huttenhower C. Biodiversity and functional genomics in the human microbiome. Trends Genet. 2013; 29(1):51-58. doi:10.1016/j.tig.2012.09.005.
14. Huttenhower C, Gevers D, Knight R, et al. Structure, function and diversity of the healthy human microbiome. Nature. 2012; 486(7402):207-214. doi:10.1038/nature11234.
15. Merga Y, Campbell B J, Rhodes J M. Mucosal barrier, bacteria and inflammatory bowel disease: possibilities for therapy. Dig Dis. 2014; 32(4):475-483. doi:10.1159/000358156.
16. Peterson L W, Artis D. Intestinal epithelial cells: regulators of barrier function and immune homeostasis. Nat Rev Immunol. 2014; 14(3):141-153. doi:10.1038/nri3608.
17. Turner J R. Intestinal mucosal barrier function in health and disease. Nat Rev Immunol. 2009; 9(11):799-809. doi:10.1038/nri2653.
18. McCauley H A, Guasch G. Three cheers for the goblet cell: maintaining homeostasis in mucosal epithelia. Trends Mol Med. 2015; 21(8):492-503. doi:10.1016/j.molmed.2015.06.003.
19. Wang S, Thacker P A, Watford M, Qiao S. Functions of Antimicrobial Peptides in Gut Homeostasis. Curr Protein Pept Sci. 2015; 16(7):582-591.
20. Macpherson A J, Geuking M B, Slack E, Hapfelmeier S, McCoy K D. The habitat, double life, citizenship, and forgetfulness of IgA. Immunol Rev. 2012; 245(1):132-146. doi:10.1111/j.1600-065X.2011.01072.x.
21. Zhu X, Messer J S, Wang Y, et al. Cytosolic HMGB1 controls the cellular autophagy/apoptosis checkpoint during inflammation. J Clin Invest. 2015; 125(3):1098-1110. doi:10.1172/JCI76344.
22. Vitali R, Stronati L, Negroni A, et al. Fecal HMGB1 Is a Novel Marker of Intestinal Mucosal Inflammation in Pediatric Inflammatory Bowel Disease. Am J Gastroenterol. 2011; 106(11):2029-2040. doi:10.1038/ajg.2011.231.
23. Palone F, Vitali R, Cucchiara S, et al. Role of HMGB1 as a suitable biomarker of subclinical intestinal inflammation and mucosal healing in patients with inflammatory bowel disease. Inflamm Bowel Dis. 2014; 20(8):1448-1457. doi:10.1097/MIB.0000000000000113.
24. Ofek I, Beachey E H. Mannose binding and epithelial cell adherence of *Escherichia coli*. Infect Immun. 1978; 22(1):247-254.
25. Zetterstrom C K, Bergman T, Rynnel-Dagoo B, et al. High Mobility Group Box Chromosomal Protein 1 (HMGB1) Is an Antibacterial Factor Produced by the Human Adenoid. Pediatr Res. 2002; 52(2):148-154. doi:10.1203/00006450-200208000-00004.
26. Mossman K L, Mian M F, Lauzon N M, et al. Cutting edge: FimH adhesin of type 1 fimbriae is a novel TLR4 ligand. J Immunol. 2008; 181(10):6702-6706.
27. Abraham S N, Baorto D M, Gao Z, et al. Survival of FimH-expressing enterobacteria in macrophages relies on glycolipid traffic. Nature. 1997; 389(6651):636-639. doi:10.1038/39376.
28. Orndorff P E, Falkow S. Organization and expression of genes responsible for type 1 piliation in *Escherichia coli*. J Bacteriol. 1984; 159(2):736-744.
29. Haiko J, Westerlund-Wikstrom B. The role of the bacterial flagellum in adhesion and virulence. Biology (Basel). 2013; 2(4):1242-1267. doi:10.3390/biology2041242.
30. Klemm P, Vejborg R M, Hancock V. Prevention of bacterial adhesion. Appl Microbiol Biotechnol. 2010; 88(2):451-459. doi:10.1007/s00253-010-2805-y.
31. Davidson N J, Fort M M, Müller W, Leach M W, Rennick D M. Chronic colitis in IL-10−/− mice: insufficient counter regulation of a Th1 response. Int Rev Immunol. 2000; 19(1):91-121.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:

1. A method of treating or preventing microbial virulence in a subject suffering from decreased high mobility group box 1 (HMGB1) protein levels and/or a deficiency in HMGB1 function, the method comprising:
   identifying decreased HMGB1 protein levels and/or a deficiency in HMGB1 function in the subject; and
   administering a composition comprising an HMGB1 polypeptide or variant or fragment thereof and a pharmaceutically acceptable carrier to the subject, wherein said administering prevents or treats microbial virulence in said subject.

2. The method of claim 1, wherein said microbe is a bacteria.

3. The method of claim 1, wherein said HMGB1 polypeptide or variant or fragment thereof is conjugated to a drug.

4. The method of claim 3, wherein said drug is an antimicrobial drug.

5. The method of claim 1, wherein the subject further suffers from a chronic inflammatory disease, an infectious disease, a metabolic disease, or a cancer.

6. The method of claim 5, wherein the subject suffers from a disease selected from the group consisting of inflammatory bowel disease, rheumatoid arthritis, non-alcoholic fatty liver disease, type II diabetes, urinary tract infection, colorectal cancer, and sepsis.

7. The method of claim 1, wherein said HMGB1 polypeptide or variant or fragment thereof binds to the motif [S/T]-x-E-x-P in a microbial protein.

8. The method of claim 1, wherein said HMGB1 polypeptide or variant or fragment thereof binds to *E. coli* FimH protein.

9. The method of claim 1, wherein said HMGB1 polypeptide or variant or fragment thereof comprises at least one amino acid change relative to wild type HMGB1.

* * * * *

```
                          SEQUENCE LISTING

<160> NUMBER OF SEQ ID NOS: 4

<210> SEQ ID NO 1
<211> LENGTH: 215
<212> TYPE: PRT
<213> ORGANISM: Homo sapiens

<400> SEQUENCE: 1

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Asp Glu Glu
            180                 185                 190

Asp Glu Glu Asp Glu Glu Glu Glu Asp Glu Glu Asp Glu Asp Glu
        195                 200                 205

Glu Glu Asp Asp Asp Asp Glu
        210                 215

<210> SEQ ID NO 2
<211> LENGTH: 45
<212> TYPE: PRT
<213> ORGANISM: Artificial sequence
<220> FEATURE:
<223> OTHER INFORMATION: synthetic

<400> SEQUENCE: 2

Thr Cys Arg Glu Glu His Lys Lys Lys His Pro Asp Ala Ser Val Asn
1               5                   10                  15

Phe Ser Glu Phe Ser Lys Lys Cys Ser Glu Arg Trp Lys Thr Met Ser
            20                  25                  30

Ala Lys Glu Lys Gly Lys Phe Glu Asp Met Ala Lys Ala
        35                  40                  45

<210> SEQ ID NO 3
<211> LENGTH: 97
```

```
<212> TYPE: PRT
<213> ORGANISM: Artificial sequence
<220> FEATURE:
<223> OTHER INFORMATION: Synthetic

<400> SEQUENCE: 3

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr Lys Lys Lys Phe Lys Asp Pro Asn Ala Pro Lys Arg
                85                  90                  95

Pro

<210> SEQ ID NO 4
<211> LENGTH: 158
<212> TYPE: PRT
<213> ORGANISM: Escherichia coli

<400> SEQUENCE: 4

Phe Ala Cys Lys Thr Ala Asn Gly Thr Ala Ile Pro Ile Gly Gly Gly
1               5                   10                  15

Ser Ala Asn Tyr Val Tyr Asn Leu Ala Pro Val Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Asn Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Val Pro Thr
145                 150                 155
```